US010781238B2

(12) United States Patent
Kim et al.

(10) Patent No.: US 10,781,238 B2
(45) Date of Patent: Sep. 22, 2020

(54) HUMAN-DERIVED FERRITIN MONOMER FRAGMENT AND FUSION POLYPEPTIDE USING SAME

(71) Applicants: KYUNGPOOK NATIONAL UNIVERSITY INDUSTRY-ACADEMIC COOPERATION FOUNDATION, Daegu (KR); KOREA INSTITUTE OF SCIENCE AND TECHNOLOGY, Seoul (KR)

(72) Inventors: So Youn Kim, Daegu (KR); Gwang-Seob Kim, Gyeongsangnam-do (KR); Jun Young Seo, Daegu (KR); In-San Kim, Daegu (KR)

(73) Assignees: KYUNGPOOK NATIONAL UNIVERSITY INDUSTRY-ACADEMIC COOPERATION FOUNDATION, Daegu (KR); KOREA INSTITUTE OF SCIENCE AND TECHNOLOGY, Seoul (KR)

(*) Notice: Subject to any disclaimer, the term of this patent is extended or adjusted under 35 U.S.C. 154(b) by 50 days.

(21) Appl. No.: 15/756,988

(22) PCT Filed: Sep. 2, 2016

(86) PCT No.: PCT/KR2016/009844
§ 371 (c)(1),
(2) Date: Mar. 2, 2018

(87) PCT Pub. No.: WO2017/039382
PCT Pub. Date: Mar. 9, 2017

(65) Prior Publication Data
US 2018/0291072 A1  Oct. 11, 2018

(30) Foreign Application Priority Data

Sep. 2, 2015 (KR) ................ 10-2015-0124467

(51) Int. Cl.
| A61K 47/65 | (2017.01) |
| A61K 47/64 | (2017.01) |
| A61K 38/17 | (2006.01) |
| A61K 49/00 | (2006.01) |
| C07K 14/47 | (2006.01) |
| C07K 14/79 | (2006.01) |
| C07K 19/00 | (2006.01) |
| C07K 14/435 | (2006.01) |
| A61K 38/00 | (2006.01) |

(52) U.S. Cl.
CPC .......... *C07K 14/47* (2013.01); *A61K 38/1709* (2013.01); *A61K 47/64* (2017.08); *A61K 47/65* (2017.08); *A61K 49/0047* (2013.01); *A61K 49/0056* (2013.01); *C07K 14/43595* (2013.01); *C07K 14/79* (2013.01); *C07K 19/00* (2013.01); *A61K 38/00* (2013.01); *C07K 2319/00* (2013.01); *C07K 2319/21* (2013.01); *C07K 2319/60* (2013.01)

(58) Field of Classification Search
None
See application file for complete search history.

(56) References Cited

U.S. PATENT DOCUMENTS 7,097,841 B2 * 8/2006 Carter .................... A61K 39/21
424/134.1
2013/0142732 A1  6/2013 Lee et al.
2016/0060307 A1  3/2016 Jun et al.

FOREIGN PATENT DOCUMENTS

| KR | 10-1189192 B1 | 10/2012 |
| KR | 10-2013-0062168 A | 6/2013 |
| KR | 10-2014-0085371 A | 7/2014 |
| KR | 10-2014-0101319 A | 8/2014 |
| KR | 10-1477123 B1 | 12/2014 |

OTHER PUBLICATIONS

KR20110140014 translation: 17 pages. (retrieved from the internet on Aug. 22, 2019). (Year: 2011).*
International Search Report for PCT/KR2016/009844 dated Dec. 1, 2016 from Korean Intellectual Property Office.

* cited by examiner

Primary Examiner — Marsha Tsay
(74) Attorney, Agent, or Firm — Revolution IP, PLLC

(57) ABSTRACT

Disclosed are a human-derived ferritin monomer fragment and a fusion polypeptide using the same, and more particularly, to a human-derived ferritin of which a portion of a fourth loop and a fifth helix of the ferritin monomer fragment are removed, and a fusion polypeptide in which a polypeptide or a protein is fused to an N-terminus or a C-terminus of the ferritin monomer fragment.

4 Claims, 8 Drawing Sheets

Specification includes a Sequence Listing.

[FIG. 1]
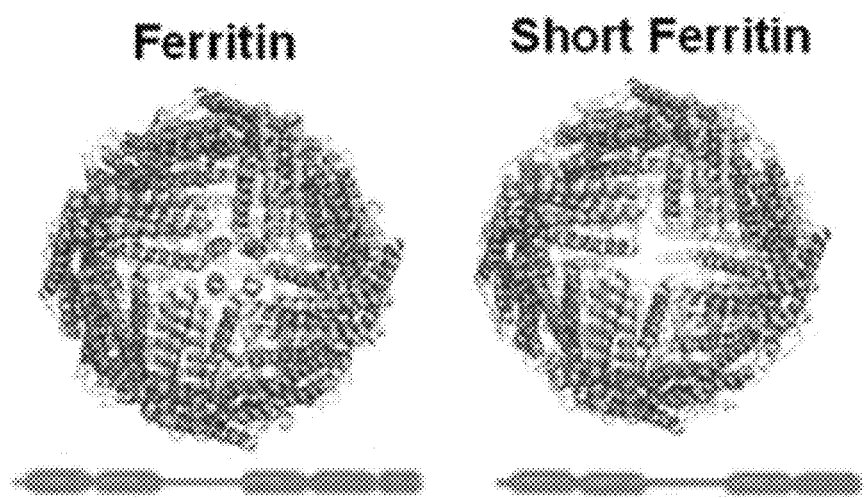
[FIG. 2]
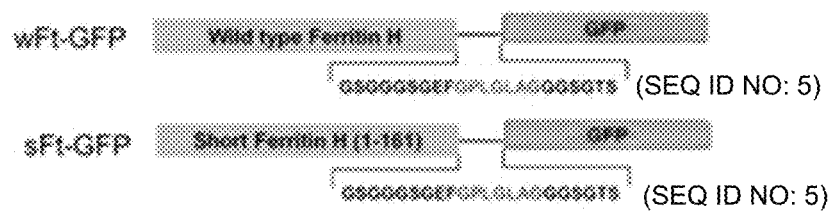
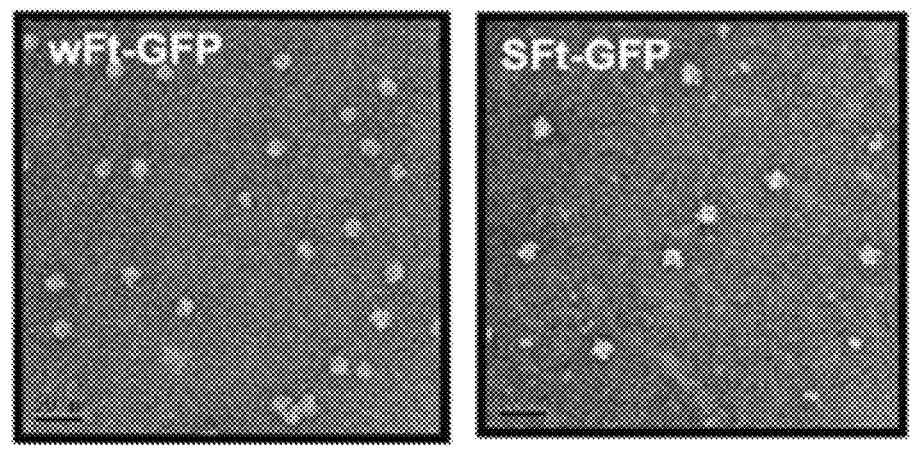

[FIG. 3]
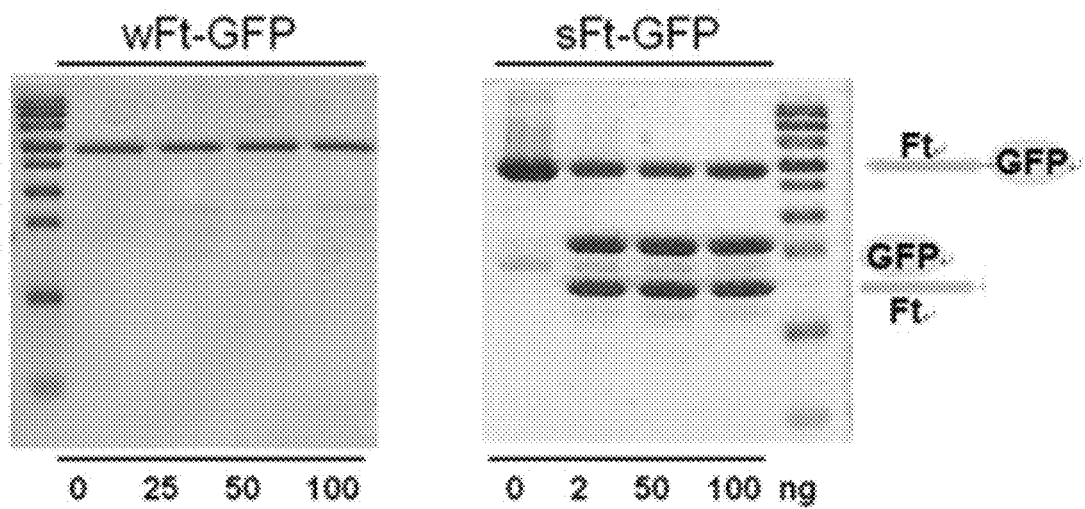
[FIG. 4]
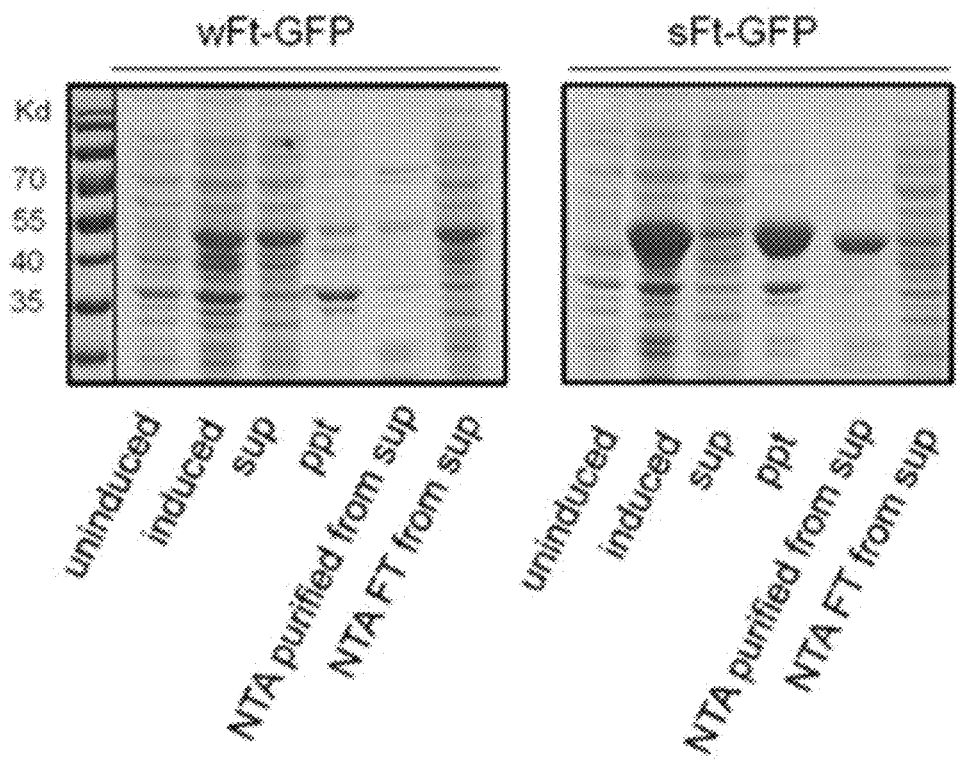

[FIG. 5]
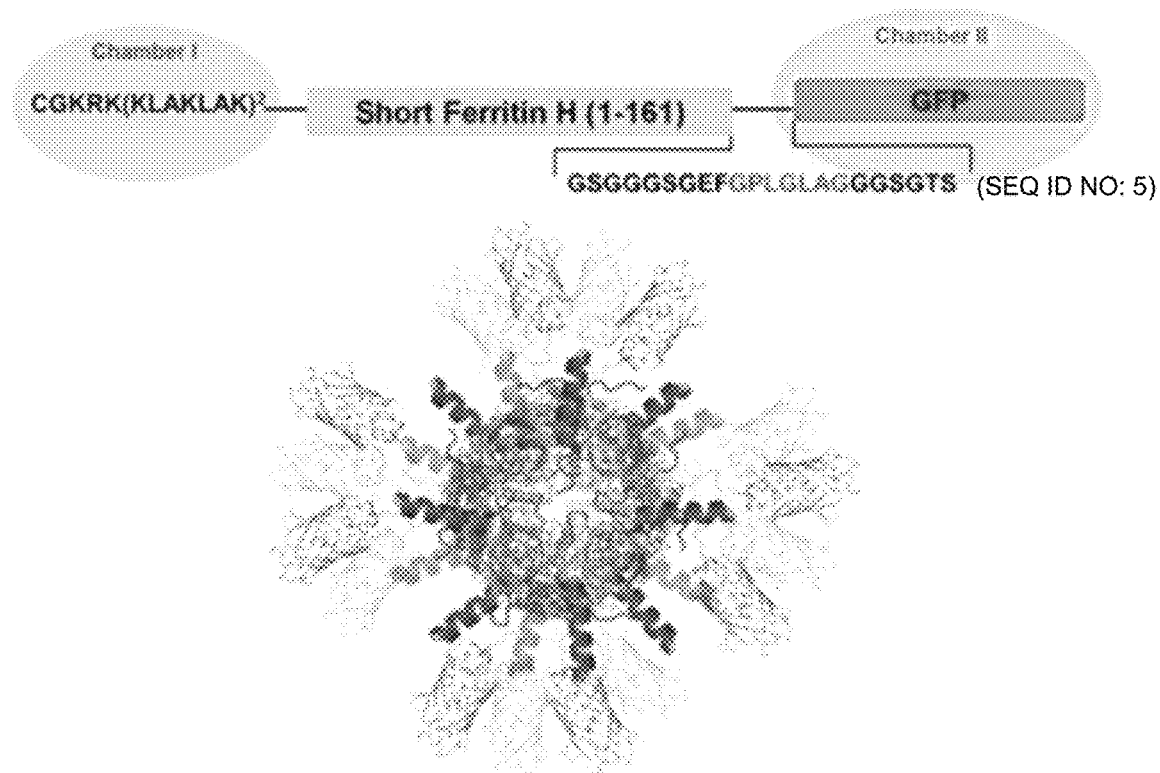

[FIG. 6]
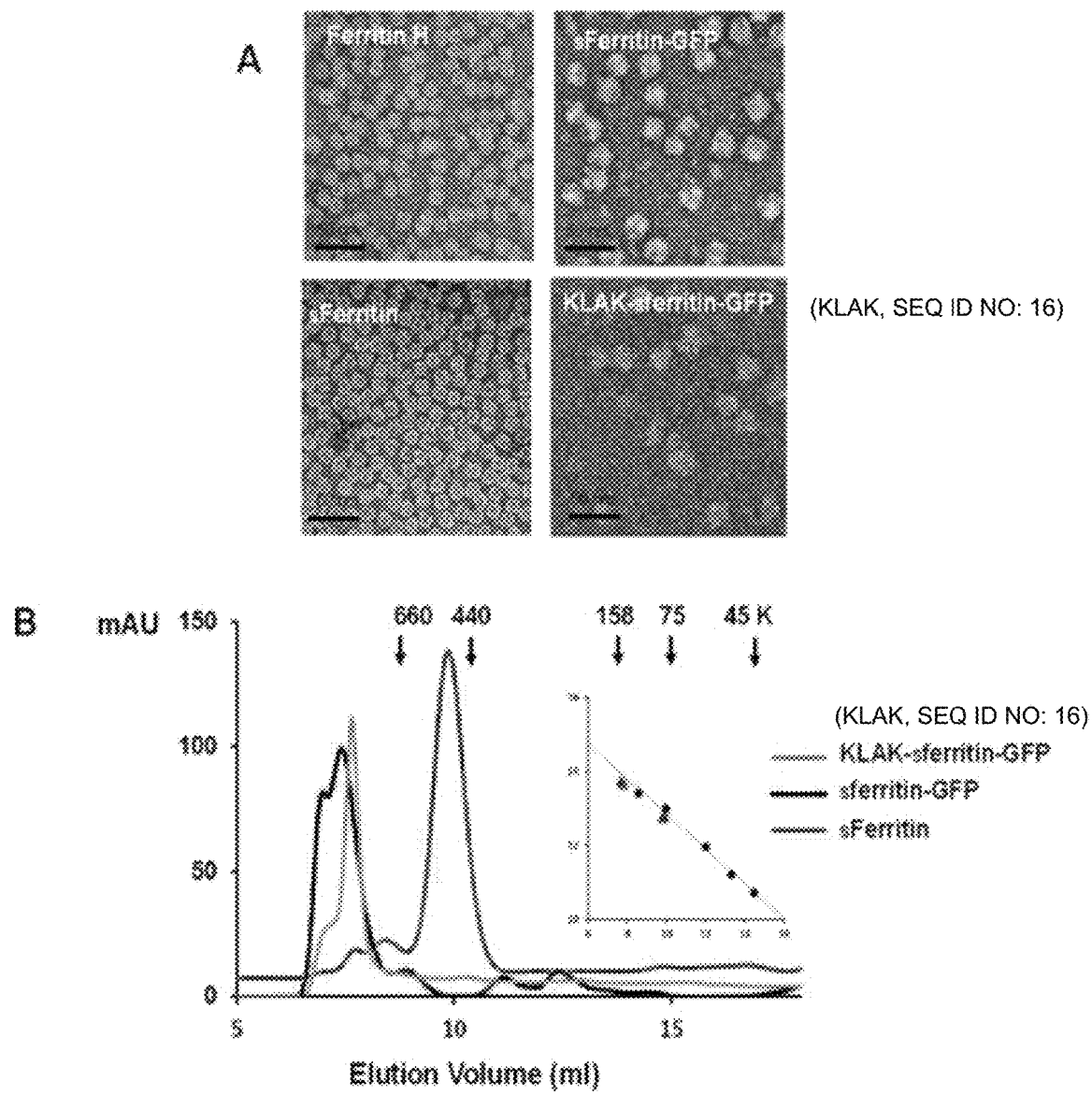

[FIG. 7]
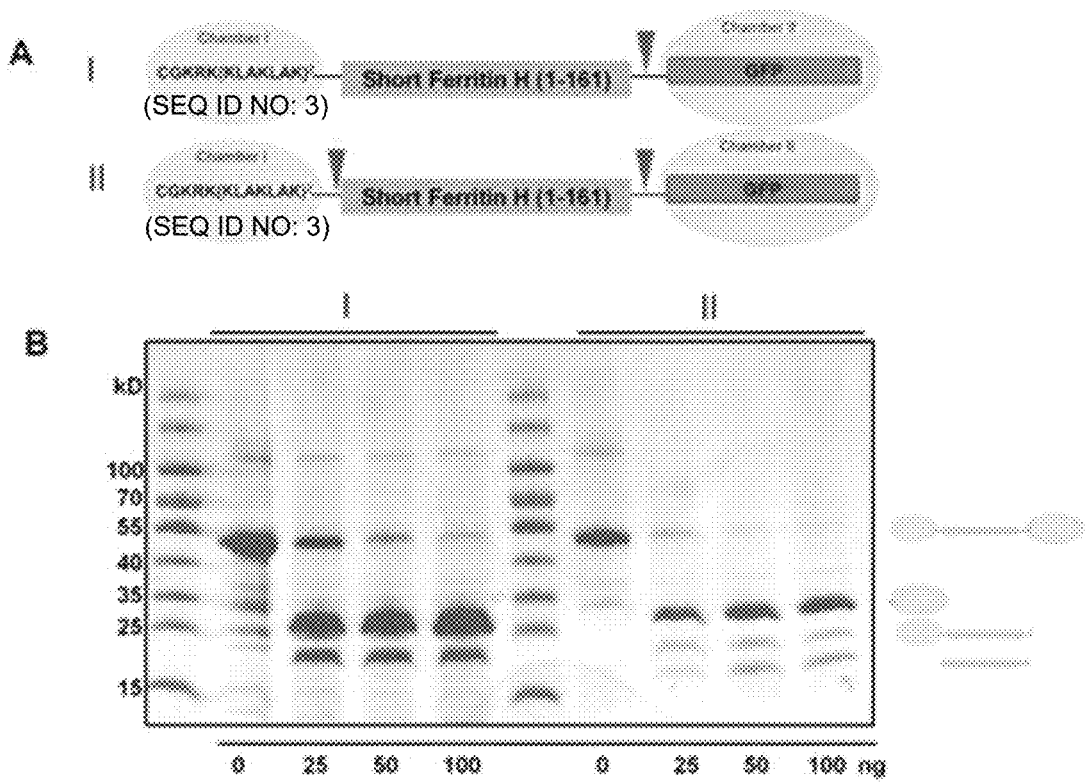

[FIG. 8]
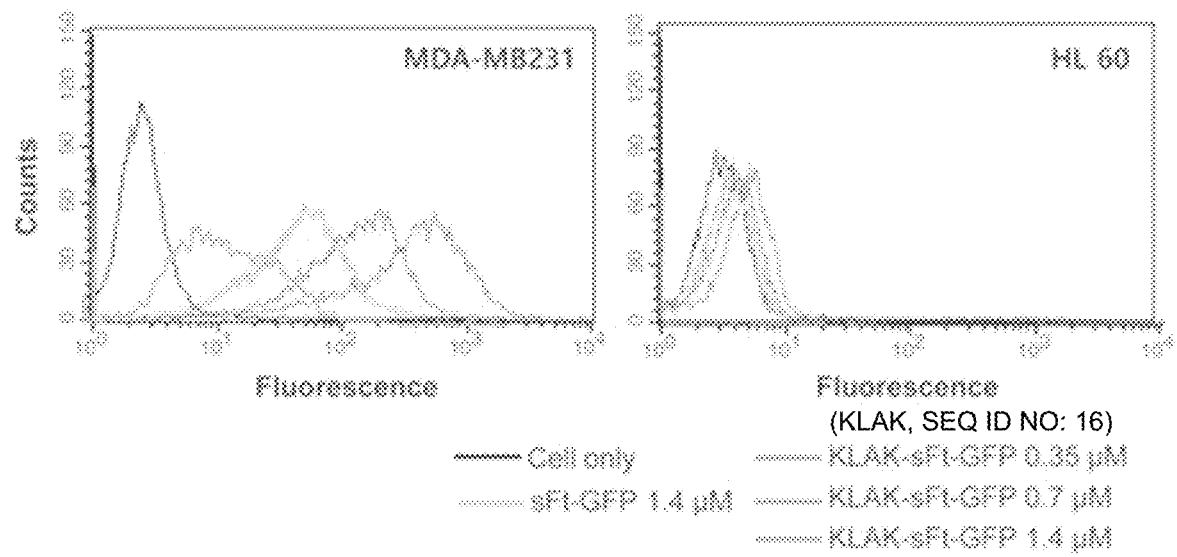
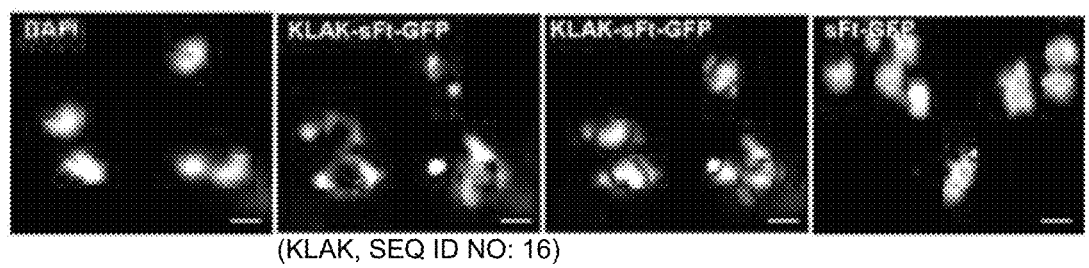
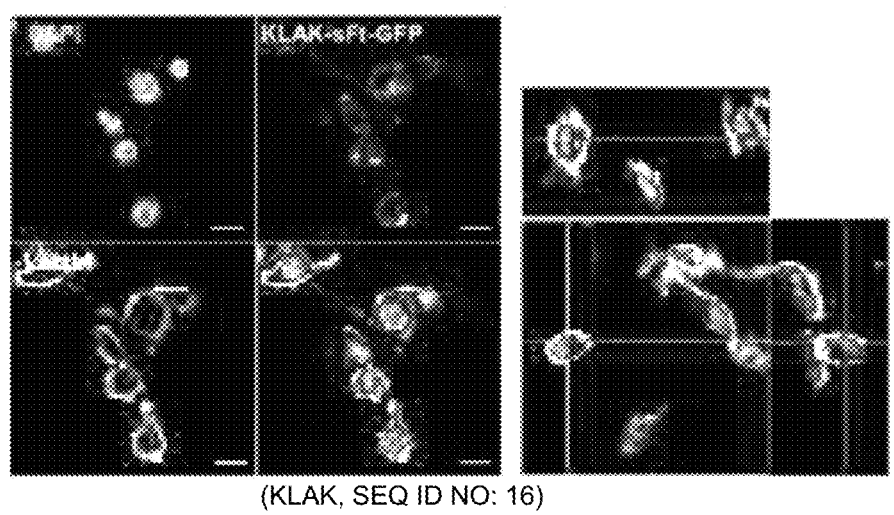

[FIG. 9]
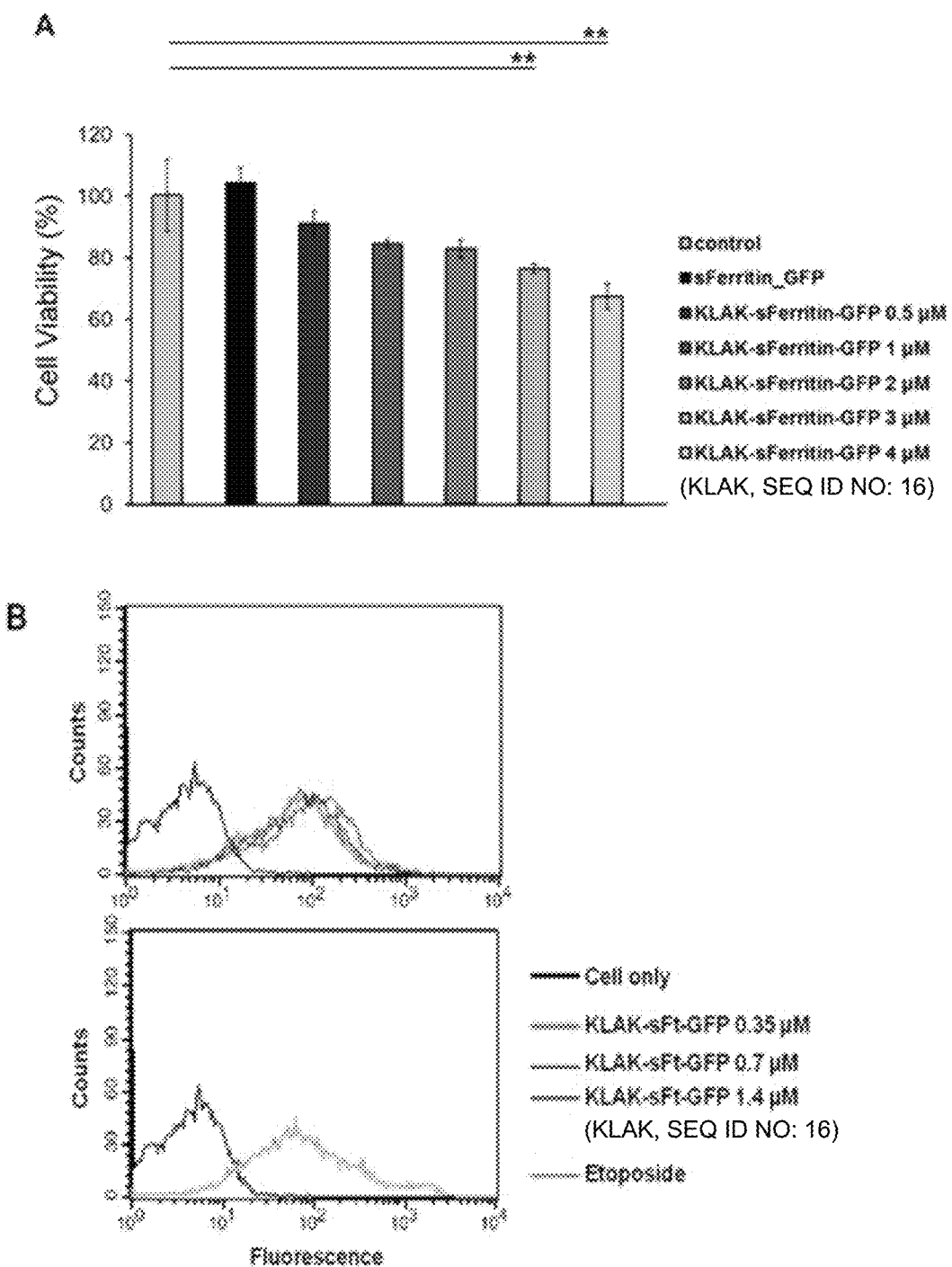

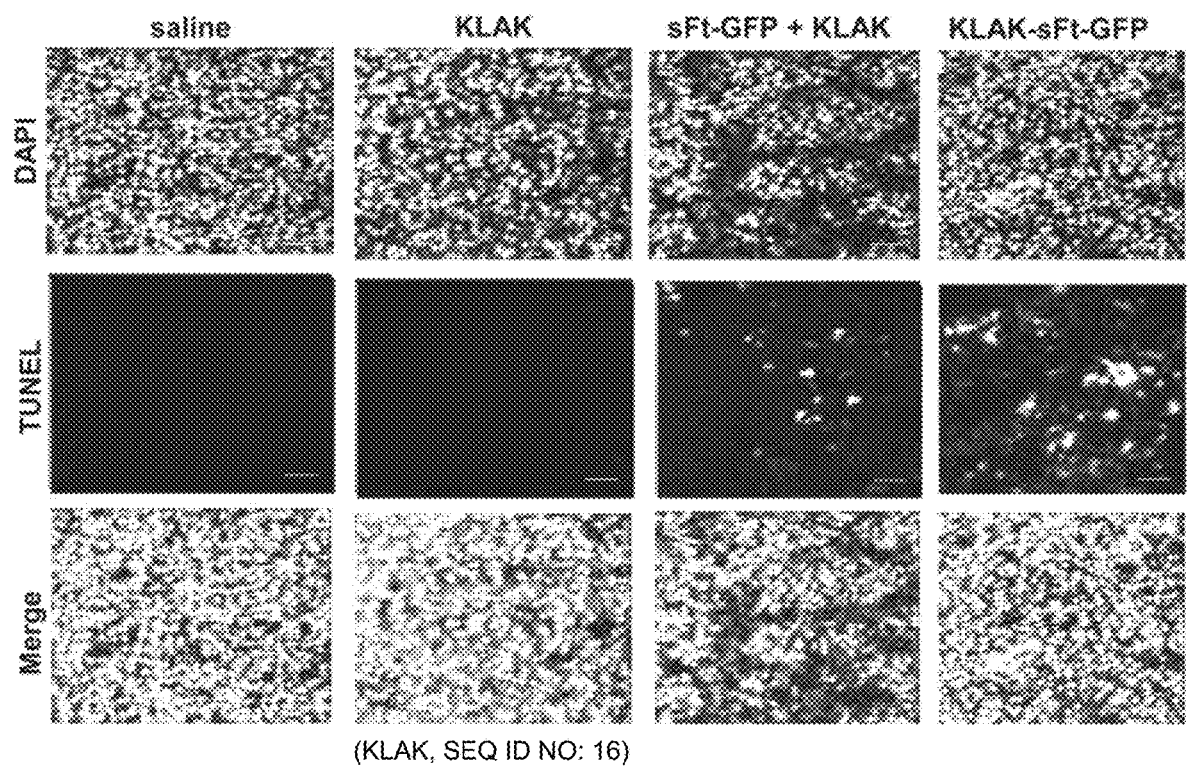
[FIG. 10]
(KLAK, SEQ ID NO: 16)

HUMAN-DERIVED FERRITIN MONOMER FRAGMENT AND FUSION POLYPEPTIDE USING SAME

TECHNICAL FIELD

The present disclosure relates to a human-derived ferritin monomer fragment and a fusion polypeptide using the same, and more particularly, to a ferritin monomer fragment of which a portion of a fourth loop and a fifth helix of a human-derived ferritin are removed and a fusion polypeptide in which a polypeptide or a protein is fused to an N-terminus or a C-terminus of the ferritin monomer fragment.

BACKGROUND ART

The present application claims the benefit of Korean Patent Application No. 10-2015-0124467, filed on Sep. 2, 2015, in the Korean Intellectual Property Office, and the entire disclosure of the specification of the claimed application is a reference to the present application.

A protein cage is a protein capable of forming a macromolecule that is tens to hundreds of times the molecular weight of monomers due to the precise self-assembly nature of low-molecular weight monomers. In nature, a viral capsid protein, ferritin, a heat shock protein, a Dps protein, and the like correspond to the protein cage, and each monomer constituting the case has very regular and precise interaction with adjacent monomers. Here, the interior of the case is an empty structure. Since such a protein cage has a property of a container or the like, the protein cage has a characteristic that the inside and the outside thereof are isolated. In this regard, the protein cage is frequently used in the medical field as a drug delivery system.

In the field of the protein cage-mediated transport, a viral vector and a non-viral vector have been actively studied. To date, adenovirus has been extensively studied as a viral vector while ferritin, a heat shock protein, or the like has been studied as a non-viral vector. However, there has been an in vivo safety issue with a viral vector in the related art due to the genes possessed by the virus itself.

Ferritin is a type of intracellular proteins that store and release iron. Ferritin is generally in the form of a hollow globular cage in a living body, and such a cage consists of 24 subunits, wherein each subunit is divided into a heavy chain and a light chain depending on a sequence thereof.

Based on the related art, the present inventors prepared a fusion polypeptide to which a polypeptide targeting a specific receptor at an N-terminus of a human-derived ferritin monomer was fused, thereby providing a target-oriented protein cage (KR Application No. 10-2013-0166241), and also prepared a fusion polypeptide to which a polypeptide targeting a specific receptor at a fourth loop of a human-derived ferritin monomer and/or an N-terminus of a human-derived ferritin monomer was fused, thereby providing a target-oriented protein cage having significantly improved binding affinity to the receptor (KR Application No. 10-2014-0015142).

However, when a polypeptide was fused to the fourth loop of a ferritin monomer, a steric hindrance occurred due to the fifth helix present in wild-type human-derived ferritin so that there was a limitation in size of a polypeptide that can be fused. In addition, when a polypeptide or a protein having a large molecular weight was fused to a C-terminus of human-derived ferritin, it has been found that a protein cage was not formed due to a steric hindrance, or that a screening effect was caused by a fused polypeptide or protein so that there was no desired physiological activity of the fused polypeptide or protein.

Therefore, to address these problems above, there is a need for developing a drug delivery platform that has a structurally relieved screening effect and has no problem in the formation of the cage, even if a peptide or protein having a large molecular weight was fused to the N-terminus of the ferritin monomer as well as the C-terminus of the ferritin monomer.

DETAILED DESCRIPTION OF THE INVENTION

Technical Problem

In this regard, the present inventors prepared a ferritin monomer fragment (i.e., short ferritin, sFt) of which a portion of a fourth loop and a fifth helix of a human-derived ferritin monomer are removed. Even if polypeptide or a protein having a large molecular weight is fused a C-terminus of the ferritin monomer fragment, a ferritin cage may be formed due to the self-assembly capability of the ferritin monomer fragment. Compared to a wild-type ferritin monomer, various advantages including a considerably alleviated steric screening effect of the ferritin monomer fragment have been found, thereby completing the present disclosure.

Therefore, there is provided a human-derived ferritin monomer fragment having an amino acid sequence represented by SEQ ID NO: 2.

There is also provided a fusion polypeptide in which a polypeptide or a protein is fused at a C-terminus, an N-terminus, or both C-terminus and N-terminus of the human-derived ferritin monomer fragment.

There is also provided a polynucleotide encoding the human-derived ferritin monomer fragment.

There is also provided an expression vector including the polynucleotide.

There is also provided a transformant transformed with the expression vector.

There is also provided a protein cage including the fusion polypeptide.

There is also provided a drug delivery system including a fusion polypeptide in which a ligand peptide capable of binding to an antibody or a cell receptor is fused to a C-terminus, an N-terminus, or both C-terminus and N-terminus of the ferritin monomer fragment.

There is also provided a pharmaceutical composition for treating cancer including, as an active ingredient, a fusion polypeptide in which a pro-apoptotic peptide or a pro-apoptotic protein is fused to a C-terminus, an N-terminus, or both C-terminus and N-terminus of the ferritin monomer fragment.

There is also provided a pharmaceutical composition for treating cancer consisting of a fusion polypeptide in which a pro-apoptotic peptide or a pro-apoptotic protein is fused to a C-terminus, an N-terminus, or both C-terminus and N-terminus of the ferritin monomer fragment.

There is also provided a pharmaceutical composition for treating cancer essentially consisting of a fusion polypeptide in which a pro-apoptotic peptide or a pro-apoptotic protein is fused to a C-terminus, an N-terminus, or both C-terminus and N-terminus of the ferritin monomer fragment.

There is also provided a bioimaging system including a fusion polypeptide in which a fluorescent protein is fused to a C-terminus, an N-terminus, or both C-terminus and N-terminus of the ferritin monomer fragment.

There is also provided use of a fusion polypeptide for preparing a cancer therapeutic agent, the fusion polypeptide including a pro-apoptotic peptide or a pro-apoptotic protein that is fused to a C-terminus, an N-terminus, or both C-terminus and N-terminus of the ferritin monomer fragment.

There is also provided a method of treating cancer, the method including: administering an effective amount of a composition including, as an active ingredient, a fusion polypeptide, to an individual in need thereof, wherein the fusion polypeptide includes a pro-apoptotic peptide or a pro-apoptotic protein that is fused to a C-terminus, an N-terminus, or both C-terminus and N-terminus of the ferritin monomer fragment.

There is also provided a method of treating cancer, the method including: administering an effective amount of a composition including, as an active ingredient, a fusion polypeptide, to an individual in need thereof, wherein the fusion polypeptide consists of a pro-apoptotic peptide or a pro-apoptotic protein that is fused to a C-terminus, an N-terminus, or both C-terminus and N-terminus of the ferritin monomer fragment.

There is also provided a method of treating cancer, the method including: administering an effective amount of a composition including, as an active ingredient, a fusion polypeptide, to an individual in need thereof, wherein the fusion polypeptide essentially consists of a pro-apoptotic peptide or a pro-apoptotic protein that is fused to a C-terminus, an N-terminus, or both C-terminus and N-terminus of the ferritin monomer fragment.

Technical Solution

To achieve the technical problems of the present disclosure, the present disclosure provides a human-derived ferritin monomer fragment including an amino acid sequence represented by SEQ ID NO: 2.

To achieve the technical problems of the present disclosure, the present disclosure provides a fusion polypeptide in which a peptide or a protein is fused to a C-terminus, an N-terminus, or both C-terminus and N-terminus of the human-derived ferritin monomer fragment.

To achieve the technical problems of the present disclosure, the present disclosure provides a polynucleotide encoding the human-derived ferritin monomer fragment.

To achieve the technical problems of the present disclosure, the present disclosure provides an expression vector including the polynucleotide.

To achieve the technical problems of the present disclosure, the present disclosure provides a transformant transformed with the expression vector.

To achieve the technical problems of the present disclosure, the present disclosure provides a protein cage including the fusion polypeptide.

To achieve the technical problems of the present disclosure, the present disclosure provides a drug delivery system including a fusion polypeptide in which a ligand peptide capable of binding to an antibody or a cell receptor is fused to a C-terminus, an N-terminus, or both C-terminus and N-terminus of the ferritin monomer fragment.

To achieve the technical problems of the present disclosure, the present disclosure provides a pharmaceutical composition for treating cancer including, as an active ingredient, a fusion polypeptide in which a pro-apoptotic peptide or a pro-apoptotic protein is fused to a C-terminus, an N-terminus, or both C-terminus and N-terminus of the ferritin monomer fragment.

To achieve the technical problems of the present disclosure, the present disclosure provides a pharmaceutical composition for treating cancer consisting of a fusion polypeptide in which a pro-apoptotic peptide or a pro-apoptotic protein is fused to a C-terminus, an N-terminus, or both C-terminus and N-terminus of the ferritin monomer fragment.

To achieve the technical problems of the present disclosure, the present disclosure provides a pharmaceutical composition for treating cancer essentially consisting of a fusion polypeptide in which a pro-apoptotic peptide or a pro-apoptotic protein is fused to a C-terminus, an N-terminus, or both C-terminus and N-terminus of the ferritin monomer fragment.

To achieve the technical problems of the present disclosure, the present disclosure provides a bioimaging system including a fusion polypeptide in which a fluorescent protein is fused to a C-terminus, an N-terminus, or both C-terminus and N-terminus of the ferritin monomer fragment.

To achieve the technical problems of the present disclosure, the present disclosure provides use of a fusion polypeptide for preparing a cancer therapeutic agent, the fusion polypeptide including a pro-apoptotic peptide or a pro-apoptotic protein that is fused to a C-terminus, an N-terminus, or both C-terminus and N-terminus of the ferritin monomer fragment.

To achieve the technical problems of the present disclosure, the present disclosure provides a method of treating cancer, the method including: administering an effective amount of a composition including, as an active ingredient, a fusion polypeptide, to an individual in need thereof, wherein the fusion polypeptide includes a pro-apoptotic peptide or a pro-apoptotic protein that is fused to a C-terminus, an N-terminus, or both C-terminus and N-terminus of the ferritin monomer fragment of claim 1.

To achieve the technical problems of the present disclosure, the present disclosure provides a method of treating cancer, the method including: administering an effective amount of a composition including, as an active ingredient, a fusion polypeptide, to an individual in need thereof, wherein the fusion polypeptide consists of a pro-apoptotic peptide or a pro-apoptotic protein that is fused to a C-terminus, an N-terminus, or both C-terminus and N-terminus of the ferritin monomer fragment.

To achieve the technical problems of the present disclosure, the present disclosure provides a method of treating cancer, the method including: administering an effective amount of a composition including, as an active ingredient, a fusion polypeptide, to an individual in need thereof, wherein the fusion polypeptide essentially consists of a pro-apoptotic peptide or a pro-apoptotic protein that is fused to a C-terminus, an N-terminus, or both C-terminus and N-terminus of the ferritin monomer fragment.

Hereinafter, the present disclosure will be described in detail.

The present disclosure provides a human-derived ferritin monomer fragment including an amino acid sequence represented by SEQ ID NO: 2.

SEQ ID NO: 2 (human-derived ferritin heavy chain monomer fragment):

```
SEQ ID NO: 2 (human-derived ferritin heavy
chain monomer fragment):
MTTASTSQVR QNYHQDSEAA INRQINLELY ASYVYLSMSY

YFDRDDVALK NFAKYFLHQS HEEREHAEKL MKLQNQRGGR
```

IFLQDIKKPD CDDWESGLNA MECALHLEKN VNQSLLELHK

LATDKNDPHL CDFIETHYLN EQVKAIKELG DHVTNLRKMG A

In addition, the present inventors further prepared a human-derived ferritin light chain monomer fragment as well as a human-derived ferritin heavy chain monomer fragment. Here, to increase the solubility of a wild-type ferritin light chain monomer fragment, the amino acid was mutated. An amino acid sequence of the human-derived ferritin light chain monomer fragment having improved solubility is as follows.

```
                                        (SEQ ID NO: 11)
MSSQIRQNYS TDVEAAVNSL VNLYLQASYT YLSLGFYFDR

DDVALEGVSH FFRELAEEKR EGYERLLKMQ NQRGGRIFLQ

DIKKPAEDEW GKTPDAMKAA MALEKKLNQA LLDLHALGSA

RTDPHLCDFL ETHFLDEEVK LIKKMGDHLT NLHRLGG
```

Ferritin is a type of intracellular proteins that store and release iron. Ferritin is generally in the form of a hollow globular cage in a living body, and such a cage consists of 24 subunits, wherein each subunit is divided into a heavy chain and a light chain depending on a structure thereof.

A ferritin monomer of the present disclosure may be both heavy chain and light chain, regardless of the structure of the ferritin monomer, and preferably, may be a ferritin heavy chain, and more preferably, may be a polypeptide consisting of an amino acid sequence represented by SEQ ID NO: 1. The amino acid sequence represented by SEQ ID NO: 1 may be a heavy chain of human-derived ferritin.

The ferritin monomer may be in the form of five alpha helix structures that are sequentially connected, wherein an irregular polypeptide portion connecting the polypeptides of each of the five alpha helix structures is called a loop.

The human-derived ferritin monomer fragment having an amino acid sequence represented by SEQ ID NO: 2 may consist of one amino acid to 161 amino acids of a human-derived ferritin heavy chain including the amino acid sequence represented by SEQ ID NO: 1. That is, a short ferritin monomer fragment (short ferritin, sFt) in which a portion of a fourth loop and a fifth helix of the ferritin heavy chain monomer are removed may be prepared. Here, the amino acid sequence represented by SEQ ID NO: 1 is as follows:

```
(human-derived ferritin heavy chain monomer,
GenBank: AAA35832.1)
                                        SEQ ID NO: 1
MTTASTSQVR QNYHQDSEAA INRQINLELY ASYVYLSMSY

YFDRDDVALK NFAKYFLHQS HEEREHAEKL MKLQNQRGGR

IFLQDIKKPD CDDWESGLNA MECALHLEKN VNQSLLELHK

LATDKNDPHL CDFIETHYLN EQVKAIKELG DHVTNLRKMG

APESGLAEYL FDKHTLGDSD NES
```

The human-derived ferritin monomer fragment having the amino acid sequence represented by SEQ ID NO: 2 is a modified form in which some of the polypeptides are removed from the wild-type ferritin monomer. However, it is important to note that the inherent characteristics of ferritin that forms a protein cage by self-assembly capability of ferritin are intact while a steric hindrance is so alleviated that the limitation on the size of a peptide or a protein that can be fused to the C-terminus is eliminated. In this regard, ferritin may be an important drug delivery platform. The ferritin monomer fragment with such advantages may seem to have unique technical characteristics that have not been reported in the related art.

The present disclosure provides a fusion polypeptide in which a polypeptide or a protein is fused to the C-terminus, the N-terminus, or both C-terminus and N-terminus of the human-derived ferritin monomer fragment.

When a polypeptide or a protein having a large molecular weight is fused to the C-terminus of the wild-type ferritin monomer, the self-assembly capability of ferritin is influenced so that ferritin may fail to form a cage. In addition, when a polypeptide or a protein is fused to both C-terminus and N-terminus of the wild-type ferritin monomer, a polypeptide or a protein fused to the C-terminus may exhibit a steric screening effect so that a polypeptide or a protein fused to the N-terminus may have inhibited physiological activity or the polypeptide may not be smoothly released from a target body tissue or organ.

However, in the case of the fusion peptide using the short ferritin monomer fragment having the amino acid sequence represented by SEQ ID NO: 2, the fusion of a protein having a large molecular weight at the C-terminus of the ferritin monomer fragment may partially or completely solve the problems above, and thus, a physiological advantage that the fusion protein using the wild-type ferritin monomer fail to exhibit may be shown.

That is, in one embodiment of the present disclosure, the present inventors prepare fusion polypeptides each using the short ferritin (sFt) monomer having the amino acid sequence represented by SEQ ID NO: 2 and the wild-type ferritin (wFt), and characteristics thereof are compared.

Then, GFP which is a protein having a relatively large molecular weight is fused to a C-terminus of each of sFt and wFt, thereby preparing a sFt-GFP fusion peptide and a wFt-GFP fusion peptide. Both sFt-GFP and wFt-GFP are well expression in *E. coli* and each form a cage. However, it is confirmed that sFt-GFP is expressed about three times as much as wFt-GFP, meaning that the protein expression of sFt-GFP is excellent. Furthermore, it is confirmed that sFt-GFP is more likely to be easily cleaved by MMP-2 compared with wFt-GFP (see Example 1 and FIG. 3), and that a histidine tag attached to the N-terminus of sFt-GFP is more efficiently separated by a NTA-agarose bead compared to a histidine tag attached to the N-terminus of wFt-GFP (see Example 1 and FIG. 4).

According to the results above, the fusion peptide in which a large molecule, GFP, is bound to the C-terminus of wFt is highly dense in terms of a spatial structure so that a linker site that is to be cleaved by MMP-2 is not readily exposed, and it is determined that six histidine tags attached to the N-terminus may be substantially hindered sterically. However, in the case of sFt in which lacking of a portion of the fourth loop and the fifth helix of the wild-type ferritin monomer, even if a large molecule, GFP, is bound to the C-terminus, a cleavage of MMP-2 is easily made, and a histidine tag attached to the N-terminus is readily separated. In this regard, it is confirmed that sFt is substantially exposed in terms of a spatial structure, as compared to wFt.

By utilizing such characteristics of sFt, (i) as compared with the fusion polypeptide fused to wFt, a fusion peptide having a significantly high yield may be prepared under the same conditions, (ii) a polypeptide fused to an N-terminus or a C-terminus may be enzymatically cleaved at a desired site in the body and readily released therefrom to thereby effectively deliver a drug and the like, and (iii) even if a polypeptide or a protein is fused to both N-terminus and C-terminus, due to a low mutual screening effect, a fusion polypeptide capable of efficiently exhibiting a desired physiological activity may be prepared.

A peptide or a protein that can be fused to the C-terminus and/or the N-terminus of the human-derived ferritin monomer fragment is not particularly limited, but may be appropriately selected by one of ordinary skill in the art to achieve the desired object. Non-limiting examples of such a peptide or a protein include an antibody, which can recognize a particular protein expressed in a tissue or organ, a ligand peptide, which can specifically bind to a specific receptor in the body, a protein drug, an enzyme, a pro-apoptotic polypeptide, a pro-apoptotic protein, or a fluorescent protein.

In the present disclosure, when an antibody capable of recognizing an antigen expressed in a specific pathological tissue is fused to the ferritin monomer fragment, a drug may be effectively delivered to a desired tissue or organ. Examples of such an antibody include a polyclonal antibody, a monoclonal antibody, a chimeric antibody, a humanized antibody, a Fv-fragment, a Fab-fragment, a F(ab')$_2$-fragment, and an scFv fragment. In addition, such an antibody may include not only a whole antibody, but also a functional fragment of an antibody molecule. The whole antibody has a structure having two full-length light chains and two full-length heavy chains, wherein each of the light chains is linked to the heavy chains via a disulfide bond. The functional fragment of the antibody molecule may be a fragment with an antigen binding function, and examples thereof include Fab, F(ab'), F(ab')2, Fv, and scFv.

In the present disclosure, types of the antibody are not particularly limited, and any antibody known in the art that can recognize an antigen expressed in a tissue or organ showing a specific pathological condition may be used.

In the present disclosure, the ligand peptide may be a peptide binding to the ferritin monomer fragment and then to a receptor of a target cell so that the fusion polypeptide of the present disclosure can be delivered to the target cell. That is, any ligand capable of binding to a hormone receptor mediating a pathological condition, a cytokine receptor, or a growth factor receptor may be used.

In addition, in the present disclosure, the ligand may include the one that can occur receptor-mediated endocytosis by binding to the receptor of the target cell. Therefore, as the receptor, any receptor present in a cell and capable of occurring receptor-mediated endocytosis may be used, and as the ligand peptide, any ligand capable of specifically binding to the receptor may be used.

In the present disclosure, the protein drug may include albumin, insulin, erythropoietin, insulin growth factor, platelet-derived growth factor, modified growth factor alpha, modified growth factor beta, bone-forming protein, and a combination thereof.

In one embodiment of the present disclosure, the protein drug is generally used for the treatment of various diseases, but due to a short half-life in the body and a low absorption rate, the protein drug have limitations in achieving therapeutic effects. Likewise, due to a low absorption rate in the body, the protein drug is mostly administered by injection. However, during the injection administration, repeated administration of the drug is required since the drug protein has a short half-life in the body of about 2 to 4 hours only. Regarding a macromolecular drug, such as a protein agent, the drug may be prepared in the form of a micro/nanoparticle using a biodegradable synthetic polymer, such as poly(lactic acid) or poly(glycolic acid), with a water-in-oil emulsion. In one or more embodiments of the present disclosure, the drug may be prepared by using a complex of polymeric materials according to PEGylation using polyethylene glycol or a reaction between an anion and a cation. However, in the case of the protein drug prepared in the form of a fine particle using poly(lactic acid) or a poly(lactic acid)-glycol phase copolymer, due to hydrophobicity of the polymeric material, there is a disadvantage that the protein drug is denaturalized. Furthermore, due to acid produced when poly(lactic acid) is decomposed in the body, the pH of the protein drug is lowered, thereby promoting denaturalization and aggregation of the protein drug. Thus, there is a need for a drug delivery system capable of maintaining the physiological activity of the protein drug while maintaining a stable blood concentration in the body for a certain period of time, and in this regard, the ferritin monomer fragment of the present disclosure may be used as a useful drug delivery system as a means of solving the problems of the protein drug.

In the present disclosure, the pro-apoptotic polypeptide or the pro-apoptotic protein may belong to a drug according to a concept that the pro-apoptotic polypeptide or the pro-apoptotic protein is fused to the ferritin monomer fragment of the present disclosure so that apoptosis of cancer cells is induced and an anticancer effect is exhibited.

In the present disclosure, examples of the pro-apoptotic protein include trastuzumab, rituximab, bevacizumab, cetuximab, bortezomib, erlotinib, gefitinib, imatinib mesylate, sunitinib, L-asparaginase, triptorelin acetate, megestrol acetate, flutamide, bicalutamide, goserelin, cytochrome c, and p53 protein, but are not limited thereto.

In the present disclosure, non-limiting examples of the pro-apoptotic peptide include KLAKLAKKLAKLAK, KGGGQVGRQLAIIGDDINR (Bak BH3 peptide, SEQ ID NO: 12), LQHRAEVQIARKLQCIADQFHRLHT (Bmf BH3 peptide, SEQ ID NO: 13), and YGRELRRMS-DEFVDS (Bad BH3 peptide, SEQ ID NO: 14), but are not limited thereto. One of ordinary skill in the art will be familiar with a peptide that exhibit cytotoxicity, in addition to peptides not specifically described in the present specification.

In the present disclosure, the fluorescent protein may refer to a substance that emits light by a change in a physical condition or a chemical treatment. The fluorescent protein may be a fluorescent protein, such as a green fluorescent protein (GFP), a yellow fluorescent protein (YFP), and a red florescent protein (RFP), a photoprotein, or a luciferase, but is not limited thereto. Any fluorescent substance used in the art may be used.

In one embodiment, a fusion peptide in which a pro-apoptotic peptide consisting of an amino acid sequence represented by SEQ ID NO: 3 is fused to the N-terminus of the ferritin monomer fragment and GFP is fused to the C-terminus of the ferritin monomer fragment is prepared, and the physiological activity thereof is evaluated.

In detail, the pro-apoptotic peptide consisting of the amino acid sequence represented by SEQ ID NO: 3 at the N-terminus of the ferritin monomer fragment includes an amino acid sequence (CGKRK, SEQ ID NO: 15) that can bind to a p32 receptor which is over-expressed on a surface of a cancer cell. As a result of treating the fusion polypeptide with a cancer cell, the fusion polypeptide is smoothly uptaken into the cancer cell through the p32 receptor with the result that green fluorescence fused to the C-terminus of the ferritin monomer fragment is also observed within the cytoplasm of the cancer cell. Consequently, the induction of apoptosis is confirmed (see Example 5).

That is, even if GFP which is a protein having a large molecular weight is fused to the C-terminus of the short ferritin monomer fragment having the amino acid sequence represented by SEQ ID NO: 2, it is confirmed that the physiological activity of the polypeptide fused to the N-terminus is never inhibited and that the physiological activity of the polypeptide or the protein fused to the N-terminus or the C-terminus is normally expressed.

The present disclosure also provides a fusion polypeptide in which the peptide or the protein is fused via a linker to the C-terminus and/or the N-terminus of the human-derived ferritin monomer fragment.

The linker is for attaching the polypeptide or the protein to a specific site of the C-terminus or the N-terminus of the ferritin monomer fragment, and may consist of one amino acid to several amino acids.

In the present disclosure, the linker may preferably be a linker including an amino acid sequence that can serve as a substrate for a protein cleavage enzyme. That is, the linker may be cleaved by the protein cleavage enzyme such that the fused polypeptide or the fused protein may be dissociated from the ferritin monomer fragment and then exhibit physiological activity in the desired tissue or organ.

Types of the linker are not particularly limited, but the linker may preferably be a linker including a cleavage site with respect to urokinase, pro-urokinase, plasmin, plasminogen, TGFβ, staphylokinase, thrombin, factor IXa, factor Xa, or methalloproteinase (MMP), such as interstitial collagenase, gelatinase, or stromelysin. In addition, in one embodiment, the linker may include an amino acid sequence capable of being cleaved by MMP-2 and represented by SEQ ID NO: 5, and the activity thereof is evaluated.

The amino acid sequence represented by SEQ ID NO: 5 is as follows:

```
(linker)
                                            SEQ ID NO: 5
GSGGGSGEFGPLGLAGGGSGTS
```

When a fusion polypeptide to which a linker that can be decomposed at the N-terminus or the C-terminus ferritin monomer fragment by the enzymes above is prepared, the polypeptide or the protein capable of exhibiting physiological activity in a desired site may be smoothly released to serve as a drug delivery system.

In one embodiment, a fusion polypeptide (having an amino acid sequence represented by SEQ ID NO: 6 or 7) fused with a pro-apoptotic peptide or GFP via linker which can be cleaved by MMP-2 and has an amino acid sequence at the C-terminus or at both C-terminus and N-terminus of the ferritin monomer fragment having the amino acid sequence represented by SEQ ID NO: 2 is prepared. Then, after the fusion polypeptide forms a ferritin cage, it is evaluated whether the linker is exposed and cleaved (see Example 4). As a result, it is observed that the linker bound to the C-terminus or the N-terminus is dependent on the concentration of products produced by cleavage by MMP-2.

The amino acid sequences represented by SEQ ID NOs: 6 and 7 are as follows:

```
(pro-apoptotic peptide-ferritin monomer
fragment-linker-GFP fusion polypeptide)
                                            SEQ ID NO: 6
MGGTCGKRKKLAKLAKKLAKLAKGHMTTASTSQVRQNYHQDSEAAINRQI

NLELYASYVYLSMSYYFDRDDVALKNFAKYFLHQSHEEREHAEKLMKLQN

QRGGRIFLQDIKKPDCDDWESGLNAMECALHLEKNVQSLLELHKLATDK

NDPHLCDFIETHYLNEQVKAIKELGDHVTNLRKMGAGSGGGSGEFGPLGL

AGGGSGTSVDVSKGEELFTGVVPILVELDGDVNGHKFVSGEGEGDATYGK

LTLKFICTTGKLPVPWPTLVTTLTYGVQCFSRYPDHMKQHDFFKSAMPEG

YVQERTIFFKDDGNYKTRAEVKFEGDTLVNRIELKGIDFKEDGNILGHKL

EYNYNSHNVYITADKQKNGIKANFKIRHNIEDGGVQLADHYQQNTPIGDG

PVLLPDNHYLSTQSALSKDPNEKRDHMVLLEFVTAAGITLGMDELYK (pro-apoptotic peptide-linker-ferritin monomer
fragment-linker-GFP fusion polypeptide)
                                            SEQ ID NO: 7
MGGTCGKRKKLAKLAKKLAKLAKASGPLGLAGHMTTASTSQVRQNYHQDS

EAAINRQINLELYASYVYLSMSYYFDRDDVALKNFAKYFLHQSHEEREHA

EKLMKLQNQRGGRIFLQDIKKPDCDDWESGLNAMECALHLEKNVQSLLE

LHKLATDKNDPHLCDFIETHYLNEQVKAIKELGDHVTNLRKMGAGSGGGS

GEFGPLGLAGGGSGTSVDVSKGEELFTGVVPILVELDGDVNGHKFSVSGE

GEGDATYGKLTLKFICTTGKLPVPWPTLVTTLTYGVQCFSRYPDHMKQHD

FFKSAMPEGYVQERTIFFKDDGNYKTRAEVKFEGDTLVNRIELKGIDFKE

DGNILGHKLEYNYNSHNVYITADKQKNGIKANFKIRHNIEDGGVQLADHY

QQNTPIGDGPVLLPDNHYLSTQSALSKDPNEKRDHMVLLEFVTAAGITLG

MDELYK
```

In addition, to the fusion polypeptide of the present disclosure, a labeling substance used in a known detection method may be additionally attached. Preferably, a peptide fragment consisting of 1 to 10 histidines, i.e., a His-tag, may be used.

A histidine residue is a tag necessary for purification after expression of a recombinant protein, and is one of the most frequently used tags. The histidine residue may have high specificity and may minimally affect the structure of the desired protein. Preferably, the histidine residue may be formed in the form of a peptide consisting of 1 to 10 histidines in a consecutive manner. Here, since the histidine residue has a small size and does not significantly affect the original structure of the protein, it is convenient that there is no need to cleave a recombinant protein after formation thereof. That is, such a tag may be attached to either an N-terminus or a C-terminus of a target protein depending on a type of a vector, and a direction of the tag may be determined depending on the influence of the His-tag on the structure of the protein.

In one embodiment, the peptide or the protein fused to the ferritin monomer fragment may not interfere binding between the fusion polypeptides or binding between the fusion polypeptide and the human-derived ferritin monomer.

The fusion polypeptide of the present disclosure may be used alone without binding between the fusion polypeptides or binding between the fusion polypeptide and other ferritin monomers. However, in the same manner as in ferritin, binding between the fusion polypeptides or binding between the fusion polypeptide and other ferritin monomers may result in formation of a dimer or a trimer, formation of a cage protein using a number of monomers, or high binding specificity to other substances. In this regard, it is preferably that the polypeptide or the protein of the present disclosure does not interfere binding between the fusion polypeptides or binding between the fusion polypeptide and the human-derived ferritin monomer.

In one embodiment, a fusion polypeptide (KLAK (SEQ ID NO: 16)-sFt-GFP) in which a pro-apoptotic peptide including an amino acid sequence represented by SEQ ID NO: 3 is fused to the N-terminus of the ferritin monomer fragment including the amino acid sequence represented by SEQ ID NO: 2 and GFP having an amino acid sequence represented by SEQ ID NO: 4 is fused to the C-terminus of the same the ferritin monomer fragment is prepared, and then, it is observed whether a cage protein is formed (see Example 3). As a result, even if GFP which is a protein having a large molecular weight is fused to the C-terminus, the fusion polypeptide forms a cage.

The amino acid sequences represented by SEQ ID NOs: 3 and 4 are as follows:

```
(pro-apoptotic peptide)
                                          SEQ ID NO: 3
CGKRKKLAKLAKKLAKLAK (GFP)
                                          SEQ ID NO: 4
VDVSKGEELFTGVVPILVELDGDVNGHKFSVSGEGEGDATYGKLTLKFI

CTTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYNY

NSHNVYITADKQKNGIKANFKIRHNIEDGGVQLADHYQQNTPIGDGPVL

LPDNHYLSTQSALSKDPNEKRDHMVLLEFVTAAGITLGMDELYK
```

Although not limited thereto, the fusion polypeptide of the present disclosure may be preferably produced in large quantities according to a genetic engineering method by inserting the fusion polypeptide into a conventional vector that is designed for the purpose of expressing a foreign gene so that the fusion polypeptide can be expressed. Here, the vector may be appropriately selected depending on types and characteristics of a host cell for producing a protein, or may be newly prepared. A method of transforming the vector into a host cell and a method of producing a recombinant protein using the transformant may be easily carried out by a conventional method. That is, the selection, preparation, and transformation of the vector and the expression of the recombinant protein may be easily carried out by one of ordinary skill in the art, and some modifications of the conventional methods may be allowed in the present disclosure.

The present disclosure also provides a polynucleotide encoding the ferritin monomer fragment.

The present disclosure also provide a polynucleotide encoding the fusion polypeptide in which pro-apoptotic peptide is fused to the N-terminus of the ferritin monomer fragment and GFP is fused to the C-terminus of the same ferritin monomer fragment.

As the polynucleotide of the present disclosure, any base sequence capable of encoding the ferritin monomer fragment or the fusion polypeptide may be used. Preferably, a polynucleotide encoding the ferritin monomer fragment may be a base sequence represented by SEQ ID NO: 8, and polynucleotide encoding the fusion polypeptide may be a base sequence represented by SEQ ID NO: 9 or 10.

The polynucleotide sequences represented by SEQ ID NOs: 8 to 10 are as follows:

```
(nucleic acid sequence encoding the human-derived ferritin heavy chain
monomer fragment having the amino acid sequence represented by SEQ ID NO: 2)
                                                             SEQ ID NO: 8
ATGacgaccgcgtccacctcgcaggtgcgccagaactaccaccaggactcagaggccgccatcaac cgccagatcaacctggagctctacgcctcctacgtttacctgtccatgtcttactactttgaccgcgatgatgtggcttt gaagaactttgccaaatactttcttcaccaatctcatgaggagagggaacatgctgagaaactgatgaagctgcagaac caacgaggtggccgaatcttccttcaggatatcaagaaaccagactgtgatgactgggagagcgggctgaatgcaa tggagtgtgcattacatttggaaaaaaatgtgaatcagtcactactggaactgcacaaactggccactgacaaaaatg accccatttgtgtgacttcattgagacacattacctgaatgagcaggtgaaagccatcaaagaattgggtgaccacg tgaccaacttgcgcaagatgggagcg (nucleic acid sequence encoding the fusion polypeptide of SEQ ID NO: 6)
                                                             SEQ ID NO: 9
ATGGGCGGTACCTGCGGCAAGCGCAAGAAGCTCGCGAAGCTCGCGAA GAAGCTCGCGAAGCTCGCGAAGGGCCATATGacgaccgcgtccacctcgcaggtgcgccag aactaccaccaggactcagaggccgccatcaaccgccagatcaacctggagctctacgcctcctacgtttacctgtc catgtcttactactttgaccgcgatgatgtggctttgaagaactttgccaaatactttcttcaccaatctcatgaggaga gggaacatgctgagaaactgatgaagctgcagaaccaacgaggtggccgaatcttccttcaggatatcaagaaacca gactgtgatgactgggagagcgggctgaatgcaatggagtgtgcattacatttggaaaaaaatgtgaatcagtcacta ctggaactgcacaaactggccactgacaaaaatgaccccatttgtgtgacttcattgagacacattacctgaatgag caggtgaaagccatcaaagaattgggtgaccacgtgaccaacttgcgcaagatgggagcgGGATCCGGTG

GAGGATCTGGTGAATTCGGACCGCTGGGACTAGCCGGAGGTGGATCTGGTACT

AGTGTCGACGTGAGCAAGGGCGAGGAGCTGTTCACCGGGGTGGTGCCCATCC
```

```
TGGTCGAGCTGGACGGCGACGTAAACGGCCACAAGTTCAGCGTGTCCGGCGA

GGGCGAGGGCGATGCCACCTACGGCAAGCTGACCCTGAAGTTCATCTGCACC

ACCGGCAAGCTGCCCGTGCCCTGGCCCACCCTCGTGACCACCCTGACCTACG

GCGTGCAGTGCTTCAGCCGCTACCCCGACCACATGAAGCAGCACGACTTCTTC

AAGTCCGCCATGCCCGAAGGCTACGTCCAGGAGCGCACCATCTTCTTCAAGGA

CGACGGCAACTACAAGACCCGCGCCGAGGTGAAGTTCGAGGGCGACACCCTG

GTGAACCGCATCGAGCTGAAGGGCATCGACTTCAAGGAGGACGGCAACATCCT

GGGGCACAAGCTGGAGTACAACTACAACAGCCACAACGTCTATATCACCGCCG

ACAAGCAGAAGAACGGCATCAAGGCCAACTTCAAGATCCGCCACAACATCGAG

GACGGCGGCGTGCAGCTCGCCGACCACTACCAGCAGAACACCCCCATCGGCG

ACGGCCCCGTGCTGCTGCCCGACAACCACTACCTGAGCACCCAGTCCGCCCT

GAGCAAAGACCCCAACGAGAAGCGCGATCACATGGTCCTGCTGGAGTTCGTGA

CCGCCGCCGGGATCACTCTCGGCATGGACGAGCTGTACAAG
```

(ucleic acid sequence encoding the fusion polypeptide of SEQ ID NO: 7)

SEQ ID NO: 10

```
ATGGGCGGTACCTGCGGCAAGCGCAAGAAGCTCGCGAAGCTCGCGAA

GAAGCTCGCGAAGCTCGCGAAGGCTAGCGGACCGCTGGGACTAGCCGGACAT

ATGacgaccgcgtccacctcgcaggtgcgccagaactaccaccaggactcagaggccgccatcaaccgccag atcaacctggagctctacgcctcctacgtttacctgtccatgtcttactactttgaccgcgatgatgtggctttgaagaa ctttgccaaatactttcttcaccaatctcatgaggagagggaacatgctgagaaactgatgaagctgcagaaccaacga ggtggccgaatcttccttcaggatatcaagaaaccagactgtgatgactgggagagcgggctgaatgcaatggagtg tgcattacatttggaaaaaaatgtgaatcagtcactactggaactgcacaaactggccactgacaaaaatgacccccc atttgtgtgacttcattgagacacattacctgaatgagcaggtgaaagccatcaaagaatttgggtgaccacgtgacca acttgcgcaagatgggagcgGGATCCGGTGGAGGATCTGGTGAATTCGGACCGCTGGG

ACTAGCCGGAGGTGGATCTGGTACTAGTGTCGACGTGAGCAAGGGCGAGGAG

CTGTTCACCGGGGTGGTGCCCATCCTGGTCGAGCTGGACGGCGACGTAAACG

GCCACAAGTTCAGCGTGTCCGGCGAGGGCGAGGGCGATGCCACCTACGGCAA

GCTGACCCTGAAGTTCATCTGCACCACCGGCAAGCTGCCCGTGCCCTGGCCCA

CCCTCGTGACCACCCTGACCTACGGCGTGCAGTGCTTCAGCCGCTACCCCGAC

CACATGAAGCAGCACGACTTCTTCAAGTCCGCCATGCCCGAAGGCTACGTCCA

GGAGCGCACCATCTTCTTCAAGGACGACGGCAACTACAAGACCCGCGCCGAG

GTGAAGTTCGAGGGCGACACCCTGGTGAACCGCATCGAGCTGAAGGGCATCG

ACTTCAAGGAGGACGGCAACATCCTGGGGCACAAGCTGGAGTACAACTACAAC

AGCCACAACGTCTATATCACCGCCGACAAGCAGAAGAACGGCATCAAGGCCAA

CTTCAAGATCCGCCACAACATCGAGGACGGCGGCGTGCAGCTCGCCGACCAC

TACCAGCAGAACACCCCCATCGGCGACGGCCCCGTGCTGCTGCCCGACAACC

ACTACCTGAGCACCCAGTCCGCCCTGAGCAAAGACCCCAACGAGAAGCGCGAT

CACATGGTCCTGCTGGAGTTCGTGACCGCCGCCGGGATCACTCTCGGCATGGA

CGAGCTGTACAAG
```

The present disclosure also provides an expression vector including the polynucleotide.

The expression vector of the present disclosure may include the polynucleotide, and examples thereof include a plasmid vector, a cosmid vector, a bacteriophage vector, and a viral vector, but are not limited thereto. The expression vector the present disclosure may be a conventional expression vector used in the art, and may include, in addition to an expression regulatory sequence, such as a promoter, an operator, an initiation codon, a termination codon, a polyadenylation signal, and an enhancer (a promoter gene), a signal sequence or a leader sequence for membrane targeting or secretion. Depending on the purpose, the expression vector may be prepared variously. A promoter included in the expression vector may be a constitutive promoter or an inducible promoter. In addition, the expression vector may include a selection marker for selecting a vector-including host cell. When the expression vector is a replicable vector, a replication origin may be included.

The present disclosure also provides a transformant transformed with the expression vector.

The transformant of the present disclosure may be transformed with the expression vector, and the transformation with the expression vector may be carried out according transformation techniques known in the art. Preferably, examples of the transformation techniques include microprojectile bombardment, electroporation, calcium phosphate ($CaPO_4$) precipitation, calcium chloride ($CaCl_2$) precipitation, PEG-mediated fusion, microinjection, and liposome-mediated method, and examples of the transformant include *Escherichia coli, Bacillus subtilis, Streptomyces, Pseudomonas, Proteus mirabilis, Staphylococcus*, and *Agrobacterium tumefaciens*, but the transformation techniques and the transformant are not limited thereto.

The present disclosure also provides a protein cage including the ferritin monomer fragment or the fusion polypeptide.

The present disclosure also provides a protein cage consisting of the ferritin monomer fragment or the fusion polypeptide.

The present disclosure also provides a protein cage essentially consisting of the ferritin monomer fragment or the fusion polypeptide.

The present disclosure also provides ferritin including the ferritin monomer fragment or the fusion polypeptide.

The present disclosure also provides ferritin consisting of the ferritin monomer fragment or the fusion polypeptide.

The present disclosure also provides ferritin essentially consisting of the ferritin monomer fragment or the fusion polypeptide.

The protein cage is a cage that is formed by the precise self-assembly nature of low-molecular weight monomers and that consists of proteins having a space inside. A viral capsid protein, ferritin, a heat shock protein, a Dps protein, and the like correspond to the protein cage. The protein cage of the present disclosure may include, as a monomer constituting the protein cage, the ferritin monomer fragment or the fusion polypeptide. The protein cage of the present disclosure may consist of the ferritin monomer fragment only, the fusion polypeptide only, a combination of the ferritin monomer fragment and the fusion polypeptide or a combination of other ferritin protein monomers.

The term "self-assembly" used in the present disclosure refers to the ability of certain molecules to form a specific nanostructure by themselves without the need for external stimulation or artificial induction.

The ferritin protein of the present disclosure may be formed by the binding of ferritin protein monomers, and is generally in the form of a globular cage in a living body.

The ferritin protein of the present disclosure may be a complex protein in which the ferritin monomer fragment or the fusion polypeptide is regularly arranged as a unit, and more preferably, may be formed by three-dimensional regular arrangement of 24 ferritin monomer fragments or fusion polypeptides.

The present disclosure also provides a drug delivery system including a fusion polypeptide in which a ligand peptide capable of binding to an antibody or a cell receptor is fused to a C-terminus, an N-terminus, or both C-terminus and N-terminus of the ferritin monomer fragment including the amino acid sequence represented by SEQ ID NO: 2.

In the drug delivery system of the present disclosure, the fusion polypeptide may have an amino acid sequence represented by SEQ ID NO: 6 or 7.

The drug delivery system of the present disclosure may include the fusion polypeptide as an active ingredient.

In addition, the drug delivery system of the present disclosure may consist of the fusion polypeptide as an active ingredient.

In addition, the drug delivery system of the present disclosure may essentially consist of the fusion polypeptide as an active ingredient.

The drug may be, for example, a drug or diagnostic drug having a therapeutic or prophylactic activity for a specific disease. The specific disease may be any disease that can be treated or prevented by the drug, and preferably, may be cancer, allergy, arteriosclerosis, or asthma. The drug may be any substance known in the art, such as a chemically synthesized compound, a protein therapeutic agent, or a nucleic acid, and preferably, may be a chemically synthesized compound, a protein therapeutic agent, or a nucleic acid, such as siRNA, for treating cancer, allergy, arteriosclerosis, or asthma.

The fusion polypeptide of the present disclosure may form a protein cage, and may include a drug within the formed protein cage. In addition, the fusion polypeptide of the present disclosure may specifically bind to a molecule, a cell, or a tissue that binds to an active polypeptide exposed to the outside during the formation of the protein cage, and in this regard, the fusion polypeptide may be used as a drug delivery system that selectively delivers a drug to the molecule, the cell, or the tissue.

In addition, a drug having pharmacological activity may bind to the N-terminus and/or C-terminus of the ferritin monomer fragment, and in this case, the fusion polypeptide of the present disclosure may be used as a drug delivery system that delivers a drug directly to the ferritin monomer fragment or indirectly to the ferritin monomer fragment via a linker.

The drug delivery system of the present disclosure may target a variety of cells, tissues, or diseases depending on types of the polypeptide that is fused to the fusion polypeptide.

In one embodiment, the present inventors fuse a polypeptide of SEQ ID NO: 3, which includes an amino acid sequence (CGKRK, SEQ ID NO: 15) that can bind to a p32 receptor that is over-expressed on a surface of a cancer cell, to the N-terminus of the ferritin monomer fragment, and then, it is observed whether the fusion polypeptide is uptake into the cancer cell. As a result of FACS analysis, fluorescence microscopic analysis, and confocal microscopic Z-stack analysis, it is confirmed that the fusion polypeptide of the present disclosure is uptake into the cancer cell. That is, it is also confirmed that the fusion polypeptide of the present disclosure may be used as a platform for delivering a drug to a target cell (see Example 5).

The present disclosure also provides a pharmaceutical composition for treating cancer, including, as an active ingredient, a fusion polypeptide in which a pro-apoptotic peptide or a pro-apoptotic protein is fused to the C-terminus, the N-terminus, or both C-terminus and N-terminus of the ferritin monomer fragment having the amino acid sequence represented by SEQ ID NO: 2.

In the pharmaceutical composition of the present disclosure, the fusion polypeptide may have an amino acid sequence represented by SEQ ID NO: 6 or 7.

In one embodiment, as a result of preparing a fusion peptide in which a pro-apoptotic peptide is fused to the ferritin monomer fragment and evaluating the cytotoxicity of the prepared fusion peptide with respect to a cancer cell, it is confirmed that the fusion polypeptide induce the apoptosis of the cancer cell in a concentration-dependent manner (see Example 6).

The pharmaceutical composition of the present disclosure may include the fusion polypeptide alone, or may be formulated in a suitable form together with a pharmaceutically acceptable carrier. In addition, an excipient or a diluent may be further added to the pharmaceutical composition. The term "pharmaceutically acceptable' as used herein may be sued with a non-toxic composition that is physiologically acceptable and, when administered to humans, does not usually cause an allergic reaction, such as a gastrointestinal disorder and dizziness, or a similar reaction therewith.

The pharmaceutically acceptable carrier may include, for example, a carrier for oral administration or a carrier for parenteral administration. The carrier for oral administration may include lactose, starch, cellulose derivative, magnesium stearate, stearic acid, and the like, and furthermore, may include a variety of drug delivery substances used for oral administration to peptide preparations. In addition, the carrier for parenteral administration may include water, suitable oil, saline, aqueous glucose, glycol, and the like, and may further include a stabilizer and a preservative. A suitable stabilizer may include an antioxidant, such as sodium hydrogensulfite, sodium sulfite, or ascorbic acid. A suitable preservative may include benzalkonium chloride, methyl- or propyl-paraben, and chlorobutanol. The pharmaceutical composition of the present disclosure may further include, in addition to the substances above, a lubricant, a wetting agent, a sweetener, a flavoring agent, an emulsifying agent, or a suspending agent. Other pharmaceutically acceptable carriers and preparations may be those described in the following reference (see Remington's Pharmaceutical Sciences, 19th ed., Mack Publishing Company, Easton, Pa., 1995).

The pharmaceutical composition of the present disclosure may be administered to mammals, including humans, by any method. For example, the composition may be administered orally or parenterally. Although not limited thereto, parenteral administration methods include intravenous, intramuscular, intra-arterial, intramedullary, intrathecal, intracardiac, transdermal, subcutaneous, intraperitoneal, intranasal, enteral, topical, sublingual, or rectal administration.

The pharmaceutical composition of the present disclosure may be formulated for oral administration or parenteral administration according to the route of administration described above.

In the case of preparations for oral administration, the pharmaceutical composition of the present disclosure may be formulated in the form of powders, granules, tablets, pills, sugar tablets, capsules, liquids, gels, syrups, slurries, suspending agents, and the like, according to methods known in the art. For example, oral preparations may be obtained in the form of tablets and sugar tablets by mixing an active ingredient with a solid excipient, pulverizing the mixture, and adding a suitable adjuvant to the pulverized mixture, thereby processing the mixture into a granular mixture. Examples of the suitable excipient include a sugar, such as lactose, dextrose, sucrose, sorbital, mannitol, xylitol, erythritol, and maltitol, a starch, such as corn starch, wheat starch, rice starch, and potato starch, a cellulose-based substance, such as cellulose, methyl cellulose, sodium carboxymethyl cellulose, and hydroxypropyl methyl-cellulose, and a filler, such as gelatin and polyvinylpyrrolidone. In addition, in certain situations, cross-linked polyvinylpyrrolidone, agar, alginic acid, or sodium alginate may be used as a disintegrating agent. Furthermore, the pharmaceutical composition of the present disclosure may further include an anti-coagulant, a lubricant, a wetting agent, a flavoring agent, an emulsifier, and a preservative.

In the case of preparation for parenteral administration, the pharmaceutical composition of the present disclosure may be formulated in the form of injections, creams, lotions, external ointments, oils, moisturizers, gels, aerosols, and nasal inhalers, according to methods known in the art. These formulations are described in the document known as a prescription commonly in all pharmaceutical chemistry fields (see Remington's Pharmaceutical Science, 19th ed., Mack Publishing Company, Easton, Pa., 1995).

The total effective amount of the pharmaceutical composition of the present disclosure may be administered to a patient in a single dose, and may be administered in multiple doses by a fractionated treatment protocol over a prolonged period of time. The effective amount of the pharmaceutical composition of the present disclosure may vary depending on the severity of a disease. Preferably, the total effective amount of the pharmaceutical composition of the present disclosure to be administered in a day may be in a range of about 0.01 μg to about 10,000 mg, more preferably, about 0.1 mg to about 500 mg, per 1 kg of the patient's body weight. However, the dosage of the pharmaceutical composition is considered with a variety of factors including a formulation method, a route of administration, and a frequency of treatment, as well as age, body weight, health condition, gender, severity of disease, diet, and excretion frequency of a patient, and accordingly, the effective amount of the pharmaceutical composition to be administered into a patient is determined. In this regard, one of ordinary skill in the art will determine the appropriate effective amount of the pharmaceutical composition of the present disclosure. The formulation, route of administration, and method of administration of the pharmaceutical composition of the present disclosure are not particularly limited, so long as the effects of the present disclosure described above are exhibited.

The present disclosure also provides bioimaging system including the fusion polypeptide in which a fluorescent protein is fused to the C-terminus, the N-terminus, or both C-terminus and N-terminus of the ferritin monomer fragment having the amino acid sequence represented by SEQ ID NO: 2.

In the bioimaging system of the present disclosure, the fusion polypeptide may have an amino acid sequence represented by SEQ ID NO: 6 or 7.

The fusion polypeptide in which the fluorescent protein is fused to the ferritin monomer fragment may be used as a bioimaging system, and such a bioimaging system may measure fluorescence in a cell using a fluorescence-activated cell sorting (FACS) device or a confocal microscope, thereby delivering an in vivo imaging.

In one embodiment, a polypeptide having an amino acid sequence represented by SEQ ID NO: 3 and having an amino acid sequence that can bind to a p32 receptor which is over-expressed on a surface of a cancer cell is fused to the N-terminus of the ferritin monomer, and GFP is fused to the C-terminus of the same ferritin monomer. Then, the resulting fusion polypeptide is subjected to FACS analysis, fluorescence microscopic analysis, and confocal microscopic Z-stack analysis. As a result, green fluorescence is strongly expressed in a cancer cell so that it is confirmed that the fusion polypeptide of present disclosure may provide a bioimaging system that can be used for diagnosis of disease (see Example 5).

In particular, the fusion polypeptide of the present disclosure may freely include a drug for the treatment of disease in the ferritin cage or at the N-terminus or the C-terminus of the fusion polypeptide. At the same time, a fluorescent protein may be fused to the N-terminus or the C-terminus of the fusion polypeptide so that the fusion polypeptide may be very useful for being used for diagnosis and treatment of disease simultaneously.

The present disclosure also provides use of the fusion polypeptide for preparing a cancer therapeutic agent, the fusion polypeptide including the pro-apoptotic peptide or the pro-apoptotic protein that is fused to the C-terminus, the N-terminus, or both C-terminus and N-terminus of the ferritin monomer fragment having the amino acid sequence represented by SEQ ID NO: 2.

The present disclosure also provides a method of treating cancer, the method including: administering an effective amount of a composition including, as an active ingredient, a fusion polypeptide, to an individual in need thereof, wherein the fusion polypeptide includes a pro-apoptotic peptide or a pro-apoptotic protein that is fused to the C-terminus, the N-terminus, or both C-terminus and N-terminus of the ferritin monomer fragment having the amino acid sequence represented by SEQ ID NO: 2.

The present disclosure also provides a method of treating cancer, the method including: administering an effective amount of a composition including, as an active ingredient, a fusion polypeptide, to an individual in need thereof, wherein the fusion polypeptide consists of a pro-apoptotic peptide or a pro-apoptotic protein that is fused to the C-terminus, the N-terminus, or both C-terminus and N-terminus of the ferritin monomer fragment having the amino acid sequence represented by SEQ ID NO: 2.

The present disclosure also provides a method of treating cancer, the method including: administering an effective amount of a composition including, as an active ingredient, a fusion polypeptide, to an individual in need thereof, wherein the fusion polypeptide essentially consists of a pro-apoptotic peptide or a pro-apoptotic protein that is fused to the C-terminus, the N-terminus, or both C-terminus and N-terminus of the ferritin monomer fragment having the amino acid sequence represented by SEQ ID NO: 2.

The term 'effective amount' as used herein refers to an amount showing, when administered to an individual, improvement, prevention, detection, or diagnostic effect of cancer. The term 'individual' as used herein refers to an animal, preferably, a mammal including a human, or refers to a cell, tissue, or organ derived from an animal. Here, the individual may be a patient requiring treatment.

The term 'treatment' as used herein refers collectively to any action that improves cancer or cancer symptoms, and for example, may include treatment or substantial prevention of disease or improvement of such cancer condition. Although not limited thereto, the treatment may include any action to alleviate, treat, or prevent one cancer symptom or most of cancer symptoms.

The term "comprising" as used herein is used interchangeably with 'including' or 'being characterized that'. In terms of the pharmaceutical composition or the method, such a term does not exclude additional substances, elements, or steps that are not mentioned. The term 'consisting of' as used herein means that additional substances, elements, or steps that are not separately described are excluded. The term 'essentially consisting of' as used herein means that, in terms of the pharmaceutical composition or the method, not only a substance or step that is already described, but also any substance or step that does not substantially affect the underlying characteristics of the substance or step that is already described, are included.

Advantageous Effects of the Invention

As described above, the fusion polypeptide in which the polypeptide or the protein is fused to the N-terminus and/or the C-terminus of the human-derived ferritin monomer fragment having the amino acid sequence represented by SEQ ID NO: 2 fusion polypeptide has excellent production efficiency, and can form a protein cage by self-assembly characteristics thereof. In this regard, an effective substance may be encapsulated within the fusion polypeptide, and due to low steric screening effect with a property of a three-dimensional structure of the fusion polypeptide, the physiological activity of the polypeptide or the protein fused to the N-terminus or the C-terminus is excellent. Thus, the fusion polypeptide may be effective for diagnosing disease or developing a therapeutic agent.

DESCRIPTION OF THE DRAWINGS

FIG. 1 a schematic diagram showing a wild-type ferritin monomer, a short ferritin monomer from which helix V is removed, and a ferritin cage of each of the wild-type ferritin monomer and the short ferritin monomer.

FIG. 2A is a schematic diagram showing a fusion peptide in which GFP is bound to a C-terminus of the short ferritin monomer (sFt-GFP) and a fusion peptide in which GFP is bound to a C-terminus of the wild-type ferritin monomer, and FIG. 2B shows the results of observing whether sFt-GFP and wFt-GFP each form a cage by TEM imaging.

FIG. 3 shows the results of SDS-PAGE analysis of the tendency of a linker to be cleaved after sFt-GFP and wFt-GFP are each cultured with MMP-2 for 1 hour at a temperature of 37° C. (FT: ferritin).

FIG. 4 shows the results of SDS-PAGE analysis of the purified fragments of each of sFt-GFP and wFt-GFP with respect to molecular weight markers (uninduced: whole cell suspension before induction of protein expression by IPTG; induced: whole cell suspension after induction of protein expression; sup: soluble cell lysate (supernatant); ppt: cell lysis precipitant; NTA purified from sup: bound fraction to NTA agarose beads from the soluble cell lysate; and NTA FT from sup: unbound fraction (flow through) to NTA agarose beads from the soluble cell lysate).

FIG. 5 is a schematic diagram showing a fusion peptide (KLAK (SEQ ID NO:16)-sFt-GFP) and a cage formed by the fusion peptide, wherein the fusion peptide includes GFP fused thereto via a linker including a pro-apoptotic peptide at the N-terminus of sFt and a sequence, which can be cleared by MMP-2, at the C-terminus of the sFt.

FIG. 6A shows the results of observing whether the wild-type ferritin, the short ferritin, sFt-GFP fusion peptide, and the KLAK (SEQ ID NO:16)-sFt-GFP fusion peptide each form a cage by TEM imaging, and FIG. 6B shows the results of SEC analysis of the case formed by each of the short ferritin, sFt-GFP fusion peptide, and the KLAK (SEQ ID NO:16)-sFt-GFP fusion peptide.

FIG. 7A is a schematic diagram showing a fusion peptide fused with GFP via a linker including an amino acid sequence, which can be cleaved by MMP-2, at the C-terminus of sFt (type I) and a fusion peptide fused with a pro-apoptotic peptide and GFP via a linker including amino acid sequences, which can be cleaved by MMP-2, at the C-terminus and the N-terminus of sFt (type II), and FIG. 7B shows the results observed after the fusion peptide type I and the fusion peptide type II are each treated with MMP-2 and the cleaved products are loaded on an SDS PAGE gel.

FIG. 8 shows the results observed after sFt-GFP fusion peptide and the KLAK (SEQ ID NO:16)-sFt-GFP fusion peptide are each treated in a cell line so that intracellular uptake of each fusion peptide is determined (A: FACS analysis results of MDA-MB-231 cell line (cells expressing a cancer-targeting peptide receptor (p32), left panel) and HL-60 cell line (control cells not expressing the p32, right panel), B: fluorescence microscopic observation results, C: confocal microscopic Z-stack analysis results).

FIG. 9A shows the MTT assay results of evaluating the cytotoxicity of the KLAK (SEQ ID NO:16)-sFt-GFP fusion peptide, and FIG. 9B shows the FACS results of evaluating the cytotoxicity of the KLAK (SEQ ID NO:16)-sFt-GFP fusion peptide.

FIG. 10 shows the results of evaluating in vivo cytotoxic activity of the KLAK (SEQ ID NO:16)-sFt-GFP fusion peptide, wherein the results are obtained by histological test using a confocal microscope on a tumor obtained through an animal experiment (Nuclear: blue; apoptotic region: red; and Scale bar=40 μm).

BEST MODE

Hereinafter, the present disclosure is described in detail.
Here, Examples below are described herein are illustrative examples of embodiments and are not intended to otherwise limit the scope of embodiments in any way.

EXPERIMENTAL METHOD

1. Preparation of a Fusion Peptide (KLAK (SEQ ID NO:16)-sFt-GFP) in which CGKRK(KLAKLAK)$_2$ (SEQ ID NO: 3) and GFP are Fused to a Short Ferritin Monomer A recombinant plasmid expressing Double Chambered Nano Cage (DCNC) was prepared by using a modified pET28 vector (Novagen). For efficient cloning, the modified pET28 vector had KpnI and NheI between NcoI/NdeI and an additional restriction enzymatic site for SpeI between EcoRI/SalI. A gene encoding a short-ferritin (sFt) heavy chain (1 to 161 amino acids) was obtained by PCR using cDNA of a human-derived ferritin heavy chain (Sino Biological Inc.), and then, inserted according to the previously reported method (ACS nano 2013, 7, (9), 7462-7471. etc) to NdeI and BamH1 sites to utilize bacteria-expression.

An oligonucleotide encoding CGKRK(KLAKLAK)$_2$ (SEQ ID NO 3) was synthesized, and then, inserted between KpnI and NheI. A signal enhanced green fluorescent protein (seGFP) gene was prepared by PCR, and then, inserted between SpeI and XhoI. A synthesized and flow linker (GSGGGSG, SEQ ID NO: 17) was inserted between BamHI and EcoRI, and an MMP-2-cleavage sequence (GPLGLAGGGSG, SEQ ID NO: 18) was synthesized and then inserted between EcoRI and SpeI. This sequence finally produced a linker having the GSGGGSGEFGPL-GLAGGGSGTS (SEQ ID NO: 5) sequence between GF and the ferritin monomer.

To insert an MMP-2 cleavage site between the N-terminus chamber and the ferritin monomer, the GPLGLAG (SEQ ID NO: 19) sequence was synthesized and then inserted between NheI and NdeI.

An sFt-GFP fusion peptide was prepared according to the same cloning method, except that the CGKRK(KLAK-LAK)$_2$ (SEQ ID NO: 3) sequence was inserted.

2. Expression and Purification of Protein

The protein was over-expressed in cells of *E. coli* BL21 (DE3). Here, the cells were cultured in an LB medium at a temperature of 37° C., and when the OD600 value reached 0.5, the expression of the cells was induced using IPTG 1 mM. Afterwards, the cells were collected through centrifugation, and then, the pellets were disrupted using a lysis buffer (20 mM Tris-HCl pH 8.0, 100 mM NaCl, 1 mM EDTA, 1% TritonX-100, 1 mM PMSF, and 0.5 mM DTT) with an ultrasonic processor. The expressed protein obtained from the cell lysates was purified according to the previously reported method using NTA agarose beads (see J. Analytical chemistry 2011, 83, (15), 5834-5843).

3. Confirmation of KLAK (SEQ ID NO:16)-sFt-GFP DCNC

Following the purification of the protein, the resulting protein was analyzed using the size exclusion chromatography (SEC, Superdex 200 10/300 GL column). Here, the oligomer state was determined by comparing an elusion volume with a standard molecular weight. A protein-elusion profile was observed by measuring the absorbance at 280 nm. TEM images were recorded using FEI Tecnai (Korea Basic Science Institute (KBSI)).

4. Cleavage of KLAK (SEQ ID NO:16)-sFt-GFP DCND by Recombinant MMP-2

Recombinant MMP-2 was purchased from R&D systems (Minneapolis, Minn., USA), and used for a cleavage test according to the manufacturer's instructions. MMP-2 was first activated by incubation with p-aminophenylmercuric acetate (APMA, 1 mM, Sigma, Saint Louis, Mo., USA) at a temperature of 37° C. for 1 hour. Activated MMP-2 (0, 25, 50, 100 ng) was then added to 20 μg of DCNC to prepare a TCBN buffer having a final volume of 40 μl (50 mM Tris-HCl, pH 7.5, 150 mM NaCl, 10 mM CaCl$_2$, and 0.05% Grij-35). After incubation at a temperature of 37° C. for 1 hour, DCNC only or DCNC reacted with MMP-2 was loaded onto 12% SDS-PAGE.

5. Evaluation of Cell Binding and Intracellular Uptake

A human breast cancer cell line, MDA-MB-231, (ATCC, Manassas, Va.), was cultured in a DMEM (high glucose) medium. To analyze the intracellular uptake of the MDA-MB-231 cells, 2×10$^5$ MDA-MB-231 cells were cultured with KLAK-sFt-GFP DCNC or sFt-GFP at a temperature of 37° C. for 1 hour. Then, the cultured MDA-MB-231 cells were washed with PBS and re-suspended, and green fluorescence of the MDA-MB-231 cells was analyzed using FACS Calibur cytometry (BD Biosciences, SanJose, Calif., USA). For microscopic analysis, the MDA-MB-231 cells were seeded into 8 chamber culture slides at a density of 1×10$^5$ cells/chamber, and then, cultured overnight for attachment. The MDA-MB-231 cells were cultured with 1.4 μM of KLAK (SEQ ID NO:16)-sFt-GFP DCNC or sFt-GFP at a temperature of 37° C. for 1 hour. The nuclei were stained with DAPI, and the slides were analyzed using a fluorescence microscope. To observe the distribution of nanoparticles in the cytoplasm, a confocal microscope (Carl Zeiss, Oberkochen, Germany) was used, and the cells were treated with lectin to stain a cell membrane for z-sectional imaging.

6. Evaluation of Cytotoxicity of KLAK (SEQ ID NO:16)-sFt-GFP DCNC

The cytotoxicity of KLAK (SEQ ID NO:16)-sFt-GFP DCNC was evaluated using the MDA-MB-231 cell line. The MDA-MB-231 cells were seeded onto a 96-well plate and cultured for 24 hours. Afterwards, the culture medium was replaced with a fresh DMEM medium containing KLAK (SEQ ID NO:16)-sFt-GFP DCNC (0.5 µM to 4 µM). As a control group, 4 µM sFt-GFP was added to a medium. After 48 hours of incubation, the cell viability of the MDA-MB-231 cells was evaluated according to MTT assay.

Whether the apoptosis was induced or not was evaluated according to FACS using Annexin V-Alexa Fluor 647 (Invitrogen) and propidium iodide (PI).

$1 \times 10^5$ MDA-MB-231 cells were cultured in a medium containing 0.35 µM, 0.7 µM, and 1.4 µM of KLAK (SEQ ID NO:16)-sFt-GFP DCNC, respectively, at a temperature of 37° C. for 24 hours. The MDA-MB-231 cells were washed with PBS and binding buffer (10 mM Tris-HCl, pH 7.4, 150 mM NaCl, 2 mM $CaCl_2$) each three times. The washed MDA-MB-231 cells were cultured with Annexin V-Alexa Fluor 647 and PI at a temperature of 37° C. for 20 minutes, and then, immediately subjected to FACS analysis. As a control group regarding the apoptosis, etoposide (50 µM, Sigma) was treated with cells and then observed.

7. Effect of KLAK (SEQ ID NO:16)-sFt-GFP DCNC on Apoptosis in Mouse Model

All animal experiments were carried out according to the instructions of the institute and the animal experiment methods approved by the Institutional Animal Care and Use Committee (IACUC) of Kyungpook National University (Authorization number: KNU 2015-0017). Here, the present inventors tried the best to minimize the pain of the animals. Female BALB/c nude mice (4 mice per group, a total of 16 mice) aged 6 to 8 weeks and having a weight of 20±3 g were used, and the MDA-MB-231 cells ($1 \times 10^6$) were infected to the right shoulder of the mice. When 100 $mm^3$ tumors were observed, 100 µL of KLAK (SEQ ID NO:16)-sFt-GFP (30 µmol/L) was administered to the mice intravenously three times a week. For comparison, the same amount of a KLAK peptide only, sFt-GFP+KLAK peptide (SEQ ID NO:16), or saline was used. After 4 times of the administration (after 9 days), the animals were euthanized with $CO_2$. The tumor tissues were removed from the animals, fixed with 4% paraformaldehyde (PFA) overnight, and then, frozen with cryosectioning. A confocal microscope (Zeiss, Germany) was used for the immunohistochemical studies. According to the manufacturer's instructions, the apoptosis was evaluated by a terminal deoxynucleotidyl transferase-mediated dUTP nick-end labeling (TUNEL) staining method.

Experimental Results (Examples)

Example 1

Preparation and Characteristics of Ferritin (Short Ferritin, sFt) Monomer

It has been verified whether ferritin, which has variously modified surfaces with peptides, chemicals, and proteins, was able to form a cage structure. To expose a ligand to the surface of the cage, two positions were frequently selected, wherein the two positions were each a short loop present between the N-terminus of the ferritin monomer and IV helix and V helix. The V helix which is located inside the cage and is bent protruded out of the case when a large protein fragment was bound to the C-terminus of the ferritin monomer.

To develop a nanoplatform that exhibits dual functionality, the present inventors removed the fifth helix of the ferritin monomer to prepare a short-ferritin (sFt) monomer (see FIG. 1), and the resulting sFT monomer was compared with a wild-type ferritin (wFt) monomer.

That is, to prepare the characteristics of sFt and wFt, GFP which is relatively large peptide was fused to a C-terminus of each of sFt and wFt, thereby preparing a sFt-GFP fusion peptide and a wFt-GFP fusion peptide (see FIG. 2A). Then, whether these two fusion peptides both formed a cage, respectively, was confirmed by transmission electro microscopy (TEM) (see FIG. 2B).

Both sFt-GFP and wFt-GFP were well expressed in *E. coli* and formed a cage, respectively. However, sFt-GFP was expressed about three times more than wFt-GFP, resulting that the protein expression of sFt-GFP was significantly excellent.

In addition, it was confirmed that sFt-GFP was more easily cleaved by MMP-2 as compared with wFt-GFP (see FIG. 3), and that a His-tag attached to the N-terminus of sFt-GFP was more efficiently separated by NTA-agarose beads as compared with a His-tag attached to the N-terminus of wFt-GFP (see FIG. 4).

According to the results above, it was determined that, since the fusion peptide in which macromolecule GFP was fused to the C-terminus of wFt had a very dense spatial structure, a linker site to be cleaved by MMP-2 was not easily exposed. In this regard, it is deemed that 6 His-tags attached to the N-terminus could be sterically screened. However, in the case of sFT in which V helix was removed from the wFT monomer, even if macromolecule GFP was fused to the C-terminus of sFT, a linker site was easily cleaved by MMP-2 and a His-tag attached to the N-terminus of sFT was easily separated. In this regard, it was confirmed that, as compared with wFt, sFT had a spatial structure that was significantly exposed.

Example 2

Preparation of Pro-Apoptotic Peptide and Fusion Peptide in which GFP was Fused to sFt According to the experimental results above, it was confirmed that sFt was available as a dual delivery system of a peptide and/or a protein and was easily cleaved by an enzyme so that the release of a fusion peptide was easily facilitated using sFT at a target site. In this regard, the present inventors prepared a fusion peptide (KLAK (SEQ ID NO:16)-sFt-GFP) in which a pro-apoptotic peptide, CGKRK(KLAKLAK)$_2$ (SEQ ID NO: 3), was fused to the N-terminus of sFt and GFP linked with a linker including a sequence that can be cleaved by MMP-2 was fused to the C-terminus of sFt (see FIG. 5).

Example 3

Test on Cage Formation of KLAK (SEQ ID NO:16)-sFt-GFP Fusion Peptide

To determine whether the KLAK (SEQ ID NO:16)-sFt-GFP fusion peptide formed a cage, the KLAK (SEQ ID NO:16)-sFt-GFP fusion peptide was observed by SEC and TEM. In addition, to compare the tendency of cage formation, wFt, sFt, and sFt-GFP fusion peptide were each observed in terms of the cage formation.

The results on this observation are shown in FIG. 6

As shown in FIG. 6A, it was confirmed that the KLAK (SEQ ID NO:16)-sFt-GFP fusion peptide formed with a cage of a certain size together with wFt, sFt, and sFt-GFP fusion peptide. It was also confirmed that KLAK (SEQ ID NO:16)-sFt-GFP fusion peptide and sFt-GFP fusion peptide each formed a cage of a similar size as compared with a cage formed by wFt and sFt.

As shown in FIG. 6B, the SEC analysis results confirm that KLAK (SEQ ID NO:16)-sFt-GFP fusion peptide and sFt-GFP fusion peptide released proteins earlier than proteins released by sFt, resulting that the cages formed by KLAK (SEQ ID NO:16)-sFt-GFP fusion peptide and sFt-GFP fusion peptide were larger than the case formed by sFT.

According to the results above, it was confirmed that, even if a peptide or a protein was fused to the N-terminus and the C-terminus of sFt, there was no problem in the cage formation.

Example 4

Linker Cleavage in KLAK (SEQ ID NO:16)-sFt-GFP Fusion Peptide by Enzyme

It was attempted to determine whether linkers linking peptides fused to KLAK (SEQ ID NO:16)-sFt-GFP fusion peptide could be exposed by an enzyme or whether these linkers could be cleaved by an enzyme. In type I fusion peptide, GFP was fused to the C-terminus of sFt via a linker having a sequence that can be cleaved by MMP-2, and in type II fusion peptide, GFT and pro-apoptotic peptide were fused to the C-terminus and the N-terminus of sFT, respectively, via the same linker (see FIG. 7A). MMP-2 was treated with these two fusion peptides, and then, observed after being loaded onto SDS PAGE gel.

The results of this observation are shown in FIG. 7B.

As shown in FIG. 7B, each linker of type I fusion peptide and type II fusion peptide was cleaved, and products generated by the linker cleavage were observed in a concentration-dependent manner. According to the results above, it was confirmed that, when a linker was used to fuse a target peptide or protein to the C-terminus and/or the N-terminus of sFt, the linker could be exposed and cleaved by an enzyme.

Therefore, by binding a linker having an amino acid sequence that can be decomposed by a specific enzyme to the C-terminus and/or the N-terminus of sFt to fuse a peptide or protein, a resulting fused peptide and protein was able to be released.

Example 5

Evaluation of Binding of KLAK (SEQ ID NO:16)-sFt-GFP Fusion Peptide to Cells and Intracellular Uptake of the Peptide A p32 receptor, which is a protein over-expressed on a surface of a specific cancer cell, was able to recognize CGKRK peptide (SEQ ID NO: 15) fused to the N-terminus of KLAK (SEQ ID NO:16)-sFt-GFP fusion peptide, and to uptake CGKRK peptide into the cytoplasm. Thus, KLAK (SEQ ID NO:16)-sFt-GFP fusion peptide was observed in consideration of binding thereof to cells and intracellular uptake thereof.

First, MDA-MB-231 cells and HL-60 cells in which p32 is not expressed were treated with KLAK (SEQ ID NO:16)-sFt-GFP fusion peptide or sFt-GFP fusion peptide, and then, cultured at a temperature of 37° C. for 1 hour. Afterwards, FACS was used to analyze whether intracellular fluorescence was expressed.

The results of this analysis are shown in FIG. 8A. As shown in FIG. 8A, in a group of cells treated with KLAK (SEQ ID NO:16)-sFt-GFP fusion peptide including CGKRK peptide at the N-terminus thereof, intracellular fluorescence was observed in a concentration-dependent manner, whereas, in a group of cells treated with sFt-GFP peptide in which GFP was fused to the C-terminus thereof, very low fluorescence was observed due to non-specific pinocytosis that caused transportation of the fusion peptide into cells. In addition, in a group of HL-60 cells, it was confirmed that, regardless of treatment with KLAK (SEQ ID NO:16)-sFt-GFP DCNC, the fusion peptide was non-specifically transported into the cells so that very low fluorescence was observed in the same manner as in a control group and a group of cells treated with sFt-GFP peptide.

In addition, MDA-MB-231 cells were treated with KLAK (SEQ ID NO:16)-sFt-GFP fusion peptide or sFt-GFP fusion peptide, and then, cultured at a temperature of 37° C. for 1 hour. Afterwards, a fluorescent microscope was used to observe the intracellular uptake of the fusion peptide.

The results of this observation are shown in FIG. 8B. As shown in FIG. 8B, green fluorescence along with nuclei (blue) was observed in a group of cells treated with KLAK (SEQ ID NO:16)-sFt-GFP fusion peptide, resulting that the fusion peptide was uptake into the cytoplasm. However, in a group of cells treated with sFt-GFP fusion peptide, only nuclei of the cells were observed without green fluorescence in the cytoplasm.

However, as a result of the confocal microscopic Z-stack analysis on the cells treated with KLAK (SEQ ID NO:16)-sFt-GFP fusion peptide, as shown in FIG. 8C, green fluorescent color was located within the cell membrane shown in red color, confirming again that the fusion peptide was uptake in the cells.

Example 6

Evaluation of Cytotoxic of KLAK (SEQ ID NO:16)-sFt-GFP Fusion Peptide

MDA-MB-231 cell line was treated with KLAK (SEQ ID NO:16)-sFt-GFP fusion peptide, culture for 48 hours, and subjected to MTT assay to analyze cell viability of the cells.

The results of the MTT assay are shown in FIG. 9A.

As shown in FIG. 9A, it was confirmed that the treatment with KLAK (SEQ ID NO:16)-sFt-GFP fusion peptide reduced cell viability in a concentration-dependent manner. However, since the cell viability was not significantly inhibited due to excessive cell division during incubation for 48 hours, an additional experiment was carried out.

That is, after KLAK (SEQ ID NO:16)-sFt-GFP fusion peptide was treated with cells, the cells were stained with Annexin V and PI, and the resulting cells were subjected to evaluation of cell viability thereof using FACS.

The results of the evaluation are shown in FIG. 9B. After KLAK (SEQ ID NO:16)-sFt-GFP fusion peptide was treated with the cells for 24 hours, the survival cells were reduced to 70%. That is, most of the dead cells were stained only with Annexin V, meaning that apoptosis was induced early. However, the extent of the apoptosis induced by KLAK (SEQ ID NO:16)-sFt-GFP fusion peptide was similar with the apoptosis induced by 50 µM of etoposide which is used as a positive control group.

In addition, a mouse heterogeneous model was used for an animal experiment carried out to confirm the apoptosis effect of KLAK (SEQ ID NO:16)-sFt-GFP DCNC. As follows, saline, KLAK peptide (SEQ ID NO:16), sFt-GFP+KLAK fusion peptide (SEQ ID NO:16), and KLAK (SEQ ID NO:16)-sFt-GFP (30 μmol/L) were intravenously administered to each of four groups.

The results of the administration are shown in FIG. 10.

As compared with other groups, a group treated with KLAK (SEQ ID NO:16)-sFt-GFP did not seem to have any influence in tumor growth. As shown in FIG. 10, a site of apoptosis increased within tumors. In addition, even if the amount of KLAK (SEQ ID NO:16)-sFt-GFP DCNC administered to the mouse was not enough to inhibit tumor growth, it was confirmed that KLAK (SEQ ID NO:16)-sFt-GFP DCNC stimulated apoptosis in tumors.

In conclusion, it was confirmed that the fusion peptide in which the pro-apoptotic peptide was fused according to the present disclosure caused the apoptosis after being uptaken into the cells.

INDUSTRIAL APPLICABILITY

The fusion polypeptide in which the polypeptide or the protein is fused to the N-terminus and/or the C-terminus of the human-derived ferritin monomer fragment having the amino acid sequence represented by SEQ ID NO: 2 has very excellent production efficiency, forms a protein cage by self-assembly, thereby enabling to encapsulate active ingredients in the protein cage. In addition, due to low steric screening effect with a property of a three-dimensional structure of the fusion polypeptide, the physiological activity of the polypeptide or the protein fused to the N-terminus or the C-terminus is also excellent. In this regard, the fusion polypeptide is highly effective in terms of industrial applicability as being useful in diagnosing disease or developing a therapeutic agent.

The invention claimed is:

1. A fusion polypeptide comprising a human-derived ferritin monomer fragment comprising the amino acid sequence of SEQ ID NO: 2, further comprising a pro-apoptotic polypeptide comprising the amino acid sequence of SEQ ID NO: 3 fused to the N-terminus of SEQ ID NO: 2 and a green fluorescent protein fused to the C-terminus of SEQ ID NO: 2.

2. The fusion polypeptide of claim 1, wherein the fusion polypeptide comprises the amino acid sequence of SEQ ID NO: 6 or 7.

3. A drug delivery system comprising the fusion polypeptide of claim 1.

4. The drug delivery system of claim 3, wherein the fusion polypeptide comprises the amino acid sequence of SEQ ID NO: 6 or 7.

* * * * *

SEQUENCE LISTING

<160> NUMBER OF SEQ ID NOS: 19

<210> SEQ ID NO 1
<211> LENGTH: 183
<212> TYPE: PRT
<213> ORGANISM: Artificial Sequence
<220> FEATURE:
<223> OTHER INFORMATION: Human ferritin heavy chain monomer

<400> SEQUENCE: 1

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180
```

<210> SEQ ID NO 2
<211> LENGTH: 161
<212> TYPE: PRT
<213> ORGANISM: Artificial Sequence
<220> FEATURE:
<223> OTHER INFORMATION: Human ferritin heavy chain monomer fragment

<400> SEQUENCE: 2

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
                100                 105                 110

Gln Ser Leu Leu Glu Leu His Lys Leu Ala Thr Asp Lys Asn Asp Pro
            115                 120                 125

His Leu Cys Asp Phe Ile Glu Thr His Tyr Leu Asn Glu Gln Val Lys
        130                 135                 140

Ala Ile Lys Glu Leu Gly Asp His Val Thr Asn Leu Arg Lys Met Gly
145                 150                 155                 160

Ala

<210> SEQ ID NO 3
<211> LENGTH: 19
<212> TYPE: PRT
<213> ORGANISM: Artificial Sequence
<220> FEATURE:
<223> OTHER INFORMATION: Pro-apoptotic peptide

<400> SEQUENCE: 3

Cys Gly Lys Arg Lys Lys Leu Ala Lys Leu Ala Lys Leu Ala Lys
1               5                   10                  15

Leu Ala Lys

<210> SEQ ID NO 4
<211> LENGTH: 240
<212> TYPE: PRT
<213> ORGANISM: Artificial Sequence
<220> FEATURE:
<223> OTHER INFORMATION: Green fluorescent protein

<400> SEQUENCE: 4

Val Asp Val Ser Lys Gly Glu Glu Leu Phe Thr Gly Val Val Pro Ile
1               5                   10                  15

Leu Val Glu Leu Asp Gly Asp Val Asn Gly His Lys Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Phe Phe Lys Asp Asp Gly Asn Tyr Lys Thr Arg Ala
                100                 105                 110

```
Glu Val Lys Phe Glu Gly Asp Thr Leu Val Asn Arg Ile Glu Leu Lys
            115                 120                 125
Gly Ile Asp Phe Lys Glu Asp Gly Asn Ile Leu Gly His Lys Leu Glu
        130                 135                 140
Tyr Asn Tyr Asn Ser His Asn Val Tyr Ile Thr Ala Asp Lys Gln Lys
145                 150                 155                 160
Asn Gly Ile Lys Ala Asn Phe Lys Ile Arg His Asn Ile Glu Asp Gly
                165                 170                 175
Gly Val Gln Leu Ala Asp His Tyr Gln Gln Asn Thr Pro Ile Gly Asp
            180                 185                 190
Gly Pro Val Leu Leu Pro Asp Asn His Tyr Leu Ser Thr Gln Ser Ala
        195                 200                 205
Leu Ser Lys Asp Pro Asn Glu Lys Arg Asp His Met Val Leu Leu Glu
210                 215                 220
Phe Val Thr Ala Ala Gly Ile Thr Leu Gly Met Asp Glu Leu Tyr Lys
225                 230                 235                 240

<210> SEQ ID NO 5
<211> LENGTH: 22
<212> TYPE: PRT
<213> ORGANISM: Artificial Sequence
<220> FEATURE:
<223> OTHER INFORMATION: Linker

<400> SEQUENCE: 5

Gly Ser Gly Gly Gly Ser Gly Glu Phe Gly Pro Leu Gly Leu Ala Gly
1               5                   10                  15
Gly Gly Ser Gly Thr Ser
            20

<210> SEQ ID NO 6
<211> LENGTH: 448
<212> TYPE: PRT
<213> ORGANISM: Artificial Sequence
<220> FEATURE:
<223> OTHER INFORMATION: Fusion polypeptide(1)

<400> SEQUENCE: 6

Met Gly Gly Thr Cys Gly Lys Arg Lys Lys Leu Ala Lys Leu Ala Lys
1               5                   10                  15
Lys Leu Ala Lys Leu Ala Lys Gly His Met Thr Thr Ala Ser Thr Ser
            20                  25                  30
Gln Val Arg Gln Asn Tyr His Gln Asp Ser Glu Ala Ala Ile Asn Arg
        35                  40                  45
Gln Ile Asn Leu Glu Leu Tyr Ala Ser Tyr Val Tyr Leu Ser Met Ser
    50                  55                  60
Tyr Tyr Phe Asp Arg Asp Asp Val Ala Leu Lys Asn Phe Ala Lys Tyr
65                  70                  75                  80
Phe Leu His Gln Ser His Glu Glu Arg Glu His Ala Glu Lys Leu Met
                85                  90                  95
Lys Leu Gln Asn Gln Arg Gly Gly Arg Ile Phe Leu Gln Asp Ile Lys
            100                 105                 110
Lys Pro Asp Cys Asp Asp Trp Glu Ser Gly Leu Asn Ala Met Glu Cys
        115                 120                 125
Ala Leu His Leu Glu Lys Asn Val Asn Gln Ser Leu Leu Glu Leu His
    130                 135                 140
Lys Leu Ala Thr Asp Lys Asn Asp Pro His Leu Cys Asp Phe Ile Glu
```

```
            145                 150                 155                 160
        Thr His Tyr Leu Asn Glu Gln Val Lys Ala Ile Lys Glu Leu Gly Asp
                        165                 170                 175

His Val Thr Asn Leu Arg Lys Met Gly Ala Gly Ser Gly Gly Gly Ser
                        180                 185                 190

Gly Glu Phe Gly Pro Leu Gly Leu Ala Gly Gly Gly Ser Gly Thr Ser
                        195                 200                 205

Val Asp Val Ser Lys Gly Glu Glu Leu Phe Thr Gly Val Val Pro Ile
                210                 215                 220

Leu Val Glu Leu Asp Gly Asp Val Asn Gly His Lys Phe Ser Val Ser
        225                 230                 235                 240

Gly Glu Gly Glu Gly Asp Ala Thr Tyr Gly Lys Leu Thr Leu Lys Phe
                        245                 250                 255

Ile Cys Thr Thr Gly Lys Leu Pro Val Pro Trp Pro Thr Leu Val Thr
                        260                 265                 270

Thr Leu Thr Tyr Gly Val Gln Cys Phe Ser Arg Tyr Pro Asp His Met
                        275                 280                 285

Lys Gln His Asp Phe Phe Lys Ser Ala Met Pro Glu Gly Tyr Val Gln
                        290                 295                 300

Glu Arg Thr Ile Phe Phe Lys Asp Asp Gly Asn Tyr Lys Thr Arg Ala
        305                 310                 315                 320

Glu Val Lys Phe Glu Gly Asp Thr Leu Val Asn Arg Ile Glu Leu Lys
                        325                 330                 335

Gly Ile Asp Phe Lys Glu Asp Gly Asn Ile Leu Gly His Lys Leu Glu
                        340                 345                 350

Tyr Asn Tyr Asn Ser His Asn Val Tyr Ile Thr Ala Asp Lys Gln Lys
                        355                 360                 365

Asn Gly Ile Lys Ala Asn Phe Lys Ile Arg His Asn Ile Glu Asp Gly
                        370                 375                 380

Gly Val Gln Leu Ala Asp His Tyr Gln Gln Asn Thr Pro Ile Gly Asp
        385                 390                 395                 400

Gly Pro Val Leu Leu Pro Asp Asn His Tyr Leu Ser Thr Gln Ser Ala
                        405                 410                 415

Leu Ser Lys Asp Pro Asn Glu Lys Arg Asp His Met Val Leu Leu Glu
                        420                 425                 430

Phe Val Thr Ala Ala Gly Ile Thr Leu Gly Met Asp Glu Leu Tyr Lys
                        435                 440                 445

<210> SEQ ID NO 7
<211> LENGTH: 456
<212> TYPE: PRT
<213> ORGANISM: Artificial Sequence
<220> FEATURE:
<223> OTHER INFORMATION: Fusion polypeptide(2)

<400> SEQUENCE: 7

Met Gly Gly Thr Cys Gly Lys Arg Lys Lys Leu Ala Lys Leu Ala Lys
        1               5                   10                  15

Lys Leu Ala Lys Leu Ala Lys Ala Ser Gly Pro Leu Gly Leu Ala Gly
                        20                  25                  30

His Met Thr Thr Ala Ser Thr Ser Gln Val Arg Gln Asn Tyr His Gln
                        35                  40                  45

Asp Ser Glu Ala Ala Ile Asn Arg Gln Ile Asn Leu Glu Leu Tyr Ala
                        50                  55                  60

Ser Tyr Val Tyr Leu Ser Met Ser Tyr Tyr Phe Asp Arg Asp Asp Val
```

```
         65                  70                  75                  80
Ala Leu Lys Asn Phe Ala Lys Tyr Phe Leu His Gln Ser His Glu Glu
                 85                  90                  95

Arg Glu His Ala Glu Lys Leu Met Lys Leu Gln Asn Gln Arg Gly Gly
                100                 105                 110

Arg Ile Phe Leu Gln Asp Ile Lys Pro Asp Cys Asp Asp Trp Glu
                115                 120                 125

Ser Gly Leu Asn Ala Met Glu Cys Ala Leu His Leu Glu Lys Asn Val
        130                 135                 140

Asn Gln Ser Leu Leu Glu Leu His Lys Leu Ala Thr Asp Lys Asn Asp
145                 150                 155                 160

Pro His Leu Cys Asp Phe Ile Glu Thr His Tyr Leu Asn Glu Gln Val
                165                 170                 175

Lys Ala Ile Lys Glu Leu Gly Asp His Val Thr Asn Leu Arg Lys Met
                180                 185                 190

Gly Ala Gly Ser Gly Gly Ser Gly Glu Phe Gly Pro Leu Gly Leu
        195                 200                 205

Ala Gly Gly Gly Ser Gly Thr Ser Val Asp Val Ser Lys Gly Glu Glu
        210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
                245                 250                 255

Tyr Gly Lys Leu Thr Leu Lys Phe Ile Cys Thr Thr Gly Lys Leu Pro
                260                 265                 270

Val Pro Trp Pro Thr Leu Val Thr Thr Leu Thr Tyr Gly Val Gln Cys
                275                 280                 285

Phe Ser Arg Tyr Pro Asp His Met Lys Gln His Asp Phe Phe Lys Ser
        290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
                325                 330                 335

Leu Val Asn Arg Ile Glu Leu Lys Gly Ile Asp Phe Lys Glu Asp Gly
                340                 345                 350

Asn Ile Leu Gly His Lys Leu Glu Tyr Asn Tyr Asn Ser His Asn Val
        355                 360                 365

Tyr Ile Thr Ala Asp Lys Gln Lys Asn Gly Ile Lys Ala Asn Phe Lys
370                 375                 380

Ile Arg His Asn Ile Glu Asp Gly Gly Val Gln Leu Ala Asp His Tyr
385                 390                 395                 400

Gln Gln Asn Thr Pro Ile Gly Asp Gly Pro Val Leu Leu Pro Asp Asn
                405                 410                 415

His Tyr Leu Ser Thr Gln Ser Ala Leu Ser Lys Asp Pro Asn Glu Lys
                420                 425                 430

Arg Asp His Met Val Leu Leu Glu Phe Val Thr Ala Ala Gly Ile Thr
        435                 440                 445

Leu Gly Met Asp Glu Leu Tyr Lys
        450                 455

<210> SEQ ID NO 8
<211> LENGTH: 483
<212> TYPE: DNA
<213> ORGANISM: Artificial Sequence
```

```
<220> FEATURE:
<223> OTHER INFORMATION: Polynucleotide incoding human ferritin heavy
      chain monomer

<400> SEQUENCE: 8
atgacgaccg cgtccacctc gcaggtgcgc cagaactacc accaggactc agaggccgcc      60
atcaaccgcc agatcaacct ggagctctac gcctcctacg tttacctgtc catgtcttac     120
tactttgacc gcgatgatgt ggctttgaag aactttgcca atactttcct tcaccaatct     180
catgaggaga gggaacatgc tgagaaactg atgaagctgc agaaccaacg aggtggccga     240
atcttccttc aggatatcaa gaaaccagac tgtgatgact gggagagcgg gctgaatgca     300
atggagtgtg cattacattt ggaaaaaaat gtgaatcagt cactactgga actgcacaaa     360
ctggccactg acaaaaatga cccccatttg tgtgacttca ttgagacaca ttacctgaat     420
gagcaggtga aagccatcaa agaattgggt gaccacgtga ccaacttgcg caagatggga     480
gcg                                                                   483

<210> SEQ ID NO 9
<211> LENGTH: 1344
<212> TYPE: DNA
<213> ORGANISM: Artificial Sequence
<220> FEATURE:
<223> OTHER INFORMATION: Polynucleotide incoding fusion polypeptide of
      sequence No.6

<400> SEQUENCE: 9
atgggcggta cctgcggcaa gcgcaagaag ctcgcgaagc tcgcgaagaa gctcgcgaag      60
ctcgcgaagg gccatatgac gaccgcgtcc acctcgcagg tgcgccagaa ctaccaccag     120
gactcagagg ccgccatcaa ccgccagatc aacctggagc tctacgcctc ctacgtttac     180
ctgtccatgt cttactactt tgaccgcgat gatgtggctt tgaagaactt tgccaaatac     240
tttcttcacc aatctcatga ggagagggaa catgctgaga actgatgaa gctgcagaac     300 caacgaggtg gccgaatctt ccttcaggat atcaagaaac cagactgtga tgactgggag     360
agcgggctga atgcaatgga gtgtgcatta catttggaaa aaaatgtgaa tcagtcacta     420
ctggaactgc acaaactggc cactgacaaa aatgaccccc atttgtgtga cttcattgag     480
acacattacc tgaatgagca ggtgaaagcc atcaaagaat gggtgacca cgtgaccaac     540 ttgcgcaaga tgggagcggg atccggtgga ggatctggtg aattcggacc gctgggacta     600
gccggaggtg gatctggtac tagtgtcgac gtgagcaagg gcgaggagct gttcaccggg     660
gtggtgccca tcctggtcga gctggacggc gacgtaaacg gccacaagtt cagcgtgtcc     720
ggcgagggcg agggcgatgc cacctacggc aagctgaccc tgaagttcat ctgcaccacc     780
ggcaagctgc ccgtgccctg gcccaccctc gtgaccaccc tgacctacgg cgtgcagtgc     840
ttcagccgct accccgacca catgaagcag cacgacttct tcaagtccgc catgcccgaa     900
ggctacgtcc aggagcgcac catcttcttc aaggacgacg gcaactacaa gacccgcgcc     960
gaggtgaagt tcgagggcga caccctggtg aaccgcatcg agctgaaggg catcgacttc    1020
aaggaggacg gcaacatcct ggggcacaag ctggagtaca actacaacag ccacaacgtc    1080
tatatcaccg ccgacaagca gaagaacggc atcaaggcca acttcaagat ccgccacaac    1140
atcgaggacg gcggcgtgca gctcgccgac cactaccagc agaacacccc catcggcgac    1200
ggccccgtgc tgctgcccga caaccactac ctgagcaccc agtccgccct gagcaaagac    1260
cccaacgaga agcgcgatca catggtcctg ctggagttcg tgaccgccgc cgggatcact    1320
```
ctcggcatgg acgagctgta caag         1344

<210> SEQ ID NO 10
<211> LENGTH: 1368
<212> TYPE: DNA
<213> ORGANISM: Artificial Sequence
<220> FEATURE:
<223> OTHER INFORMATION: Polynucleotide incoding fusion polypeptide of
      sequence No.7

<400> SEQUENCE: 10
atgggcggta cctgcggcaa gcgcaagaag ctcgcgaagc tcgcgaagaa gctcgcgaag    60
ctcgcgaagg ctagcggacc gctgggacta gccggacata tgacgaccgc gtccacctcg   120
caggtgcgcc agaactacca ccaggactca gaggccgcca tcaaccgcca gatcaacctg   180
gagctctacg cctcctacgt ttacctgtcc atgtcttact actttgaccg cgatgatgtg   240
gctttgaaga actttgccaa atactttctt caccaatctc atgaggagag gaacatgct    300
gagaaactga tgaagctgca gaaccaacga ggtggccgaa tcttccttca ggatatcaag   360
aaaccagact gtgatgactg ggagagcggg ctgaatgcaa tggagtgtgc attacatttg   420
gaaaaaaatg tgaatcagtc actactggaa ctgcacaaac tggccactga caaaaatgac   480
ccccatttgt gtgacttcat tgagacacat tacctgaatg agcaggtgaa agccatcaaa   540
gaattgggtg accacgtgac caacttgcgc aagatgggag cgggatccgg tggaggatct   600
ggtgaattcg accgctgggg actagccgga ggtggatctg gtactagtgt cgacgtgagc   660
aagggcgagg agctgttcac cggggtggtg cccatcctgg tcgagctgga cggcgacgta   720
aacggccaca gttcagcgt gtccggcgag ggcgagggcg atgccaccta cggcaagctg   780
accctgaagt tcatctgcac caccggcaag ctgcccgtgc cctggcccac cctcgtgacc   840
accctgacct acggcgtgca gtgcttcagc cgctaccccg accacatgaa gcagcacgac   900
ttcttcaagt ccgccatgcc cgaaggctac gtccaggagc gcaccatctt cttcaaggac   960
gacggcaact acaagacccg cgccgaggtg aagttcgagg gcgacaccct ggtgaaccgc  1020
atcgagctga agggcatcga cttcaaggag gacggcaaca tcctggggca caagctggag  1080
tacaactaca acagccacaa cgtctatatc accgccgaca gcagaagaa cggcatcaag  1140
gccaacttca gatccgcca caacatcgag gacggcggcg tgcagctcgc cgaccactac  1200
cagcagaaca cccccatcgg cgacggcccc gtgctgctgc ccgacaacca ctacctgagc  1260
acccagtccg ccctgagcaa agaccccaac gagaagcgcg atcacatggt cctgctggag  1320
ttcgtgaccg ccgccgggat cactctcggc atggacgagc tgtacaag              1368

<210> SEQ ID NO 11
<211> LENGTH: 157
<212> TYPE: PRT
<213> ORGANISM: Artificial Sequence
<220> FEATURE:
<223> OTHER INFORMATION: Human ferritin heavy chain monomer fragment

<400> SEQUENCE: 11

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu

```
                50              55              60
Arg Leu Leu Lys Met Gln Asn Gln Arg Gly Gly Arg Ile Phe Leu Gln
 65                  70                  75                  80

Asp Ile Lys Lys Pro Ala Glu Asp Glu Trp Gly Lys Thr Pro Asp Ala
                 85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly
145                 150                 155

<210> SEQ ID NO 12
<211> LENGTH: 33
<212> TYPE: PRT
<213> ORGANISM: Artificial Sequence
<220> FEATURE:
<223> OTHER INFORMATION: Bak BH3 peptide

<400> SEQUENCE: 12

Lys Leu Ala Lys Leu Ala Lys Lys Leu Ala Lys Leu Ala Lys Lys Gly
 1               5                  10                  15

Gly Gly Gln Val Gly Arg Gln Leu Ala Ile Ile Gly Asp Asp Ile Asn
                20                  25                  30

Arg

<210> SEQ ID NO 13
<211> LENGTH: 25
<212> TYPE: PRT
<213> ORGANISM: Artificial Sequence
<220> FEATURE:
<223> OTHER INFORMATION: Bmf BH3 peptide

<400> SEQUENCE: 13

Leu Gln His Arg Ala Glu Val Gln Ile Ala Arg Lys Leu Gln Cys Ile
 1               5                  10                  15

Ala Asp Gln Phe His Arg Leu His Thr
                20                  25

<210> SEQ ID NO 14
<211> LENGTH: 15
<212> TYPE: PRT
<213> ORGANISM: Artificial Sequence
<220> FEATURE:
<223> OTHER INFORMATION: Bad BH3 peptide

<400> SEQUENCE: 14

Tyr Gly Arg Glu Leu Arg Arg Met Ser Asp Glu Phe Val Asp Ser
 1               5                  10                  15

<210> SEQ ID NO 15
<211> LENGTH: 5
<212> TYPE: PRT
<213> ORGANISM: Artificial Sequence
<220> FEATURE:
<223> OTHER INFORMATION: Pro-apoptotic peptide

<400> SEQUENCE: 15

Cys Gly Lys Arg Lys
 1               5
```

```
<210> SEQ ID NO 16
<211> LENGTH: 4
<212> TYPE: PRT
<213> ORGANISM: Artificial Sequence
<220> FEATURE:
<223> OTHER INFORMATION: Fusion polypeptide

<400> SEQUENCE: 16

Lys Leu Ala Lys
1

<210> SEQ ID NO 17
<211> LENGTH: 7
<212> TYPE: PRT
<213> ORGANISM: Artificial Sequence
<220> FEATURE:
<223> OTHER INFORMATION: Linker

<400> SEQUENCE: 17

Gly Ser Gly Gly Gly Ser Gly
1               5

<210> SEQ ID NO 18
<211> LENGTH: 11
<212> TYPE: PRT
<213> ORGANISM: Artificial Sequence
<220> FEATURE:
<223> OTHER INFORMATION: Linker

<400> SEQUENCE: 18

Gly Pro Leu Gly Leu Ala Gly Gly Gly Ser Gly
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Linker

<400> SEQUENCE: 19

Gly Pro Leu Gly Leu Ala Gly
1               5
```